(12) United States Patent
Pacetti et al.

(10) Patent No.: US 9,295,663 B2
(45) Date of Patent: Mar. 29, 2016

(54) DRUG COATED BALLOON WITH IN-SITU FORMED DRUG CONTAINING MICROSPHERES

(75) Inventors: Stephen D. Pacetti, San Jose, CA (US); John J. Stankus, Campbell, CA (US)

(73) Assignee: Abbott Cardiovascular Systems Inc., Santa Clara, CA (US)

( * ) Notice: Subject to any disclaimer, the term of this patent is extended or adjusted under 35 U.S.C. 154(b) by 469 days.

(21) Appl. No.: 12/836,529

(22) Filed: Jul. 14, 2010

(65) Prior Publication Data

US 2012/0015019 A1 Jan. 19, 2012

(51) Int. Cl.
*A61F 13/00* (2006.01)
*A61K 31/337* (2006.01)
*A61K 31/436* (2006.01)
*A61K 31/675* (2006.01)
*A61L 29/08* (2006.01)
*A61L 29/16* (2006.01)
*A61L 31/10* (2006.01)
*A61L 31/16* (2006.01)
*A61M 25/10* (2013.01)

(52) U.S. Cl.
CPC ............. *A61K 31/337* (2013.01); *A61K 31/436* (2013.01); *A61K 31/675* (2013.01); *A61L 29/085* (2013.01); *A61L 29/16* (2013.01); *A61L 31/10* (2013.01); *A61L 31/16* (2013.01); *A61M 25/1029* (2013.01); *A61L 2300/416* (2013.01); *A61L 2300/606* (2013.01); *A61L 2420/02* (2013.01); *A61L 2420/06* (2013.01); *A61M 2025/105* (2013.01); *A61M 2025/1031* (2013.01)

(58) Field of Classification Search
CPC . A61K 31/337; A61K 31/436; A61K 31/675; A61L 29/085; A61L 29/16; A61L 31/10; A61L 31/16; A61L 2300/416; A61L 2300/606; A61L 2420/02; A61L 2420/06; A61M 25/1029; A61M 2025/1031; A61M 2025/105

See application file for complete search history.

(56) References Cited

U.S. PATENT DOCUMENTS

| 4,014,288 | A | 3/1977 | Ludlum |
| 4,293,539 | A | 10/1981 | Ludwig et al. |
| 4,622,244 | A | 11/1986 | Lapka et al. |
| 4,897,268 | A | 1/1990 | Tice et al. |
| 4,954,298 | A | 9/1990 | Yamamoto et al. |
| 5,409,703 | A | 4/1995 | McAnalley et al. |
| 5,453,447 | A | 9/1995 | End et al. |
| 5,674,192 | A | 10/1997 | Sahatjian et al. |
| 5,731,087 | A | 3/1998 | Fan et al. |
| 5,824,048 | A | 10/1998 | Tuch |
| 5,876,743 | A | 3/1999 | Ibsen et al. |
| 6,143,037 | A | 11/2000 | Goldstein et al. |
| 6,224,794 | B1 | 5/2001 | Amsden et al. |
| 6,287,628 | B1 | 9/2001 | Hossainy et al. |
| 6,506,437 | B1 | 1/2003 | Harish et al. |
| 6,528,093 | B1 | 3/2003 | Kamei et al. |
| 6,730,064 | B2 | 5/2004 | Ragheb et al. |
| 6,767,637 | B2 | 7/2004 | Park et al. |
| 6,872,225 | B1 | 3/2005 | Rowan et al. |
| 7,048,947 | B2 | 5/2006 | Kamei et al. |
| 7,060,299 | B2 | 6/2006 | Alavattam et al. |
| 7,658,966 | B2 * | 2/2010 | Kokish .................... 427/2.1 |
| 8,211,489 | B2 * | 7/2012 | Pacetti .................. 427/2.25 |
| 2001/0051131 | A1 * | 12/2001 | Unger ..................... 424/9.5 |
| 2002/0188037 | A1 | 12/2002 | Chudzik et al. |
| 2004/0001872 | A1 | 1/2004 | Shih et al. |
| 2004/0052858 | A1 | 3/2004 | Wu et al. |
| 2004/0143321 | A1 | 7/2004 | Litvack et al. |
| 2004/0220665 | A1 | 11/2004 | Hossainy et al. |
| 2005/0025799 | A1 | 2/2005 | Hossainy et al. |
| 2005/0025803 | A1 | 2/2005 | Richard et al. |
| 2005/0112170 | A1 | 5/2005 | Hossainy et al. |
| 2005/0129727 | A1 | 6/2005 | Weber et al. |
| 2005/0192657 | A1 | 9/2005 | Colen et al. |
| 2005/0197294 | A1 | 9/2005 | Gaich et al. |
| 2005/0208093 | A1 | 9/2005 | Glauser et al. |
| 2005/0209688 | A1 | 9/2005 | Falotico et al. |
| 2006/0035854 | A1 | 2/2006 | Goldstein et al. |
| 2006/0121080 | A1 | 6/2006 | Lye et al. |
| 2006/0182873 | A1 | 8/2006 | Klisch et al. |
| 2006/0188543 | A1 * | 8/2006 | Feng ....................... 424/423 |
| 2006/0212106 | A1 | 9/2006 | Weber et al. |
| 2006/0224237 | A1 | 10/2006 | Furst et al. |
| 2007/0020319 | A1 | 1/2007 | Bougherara |
| 2007/0065481 | A1 | 3/2007 | Chudzik et al. |
| 2007/0110787 | A1 | 5/2007 | Hossainy et al. |
| 2007/0148251 | A1 | 6/2007 | Hossainy et al. |
| 2007/0258903 | A1 | 11/2007 | Kleiner et al. |
| 2007/0292495 | A1 | 12/2007 | Ludwig et al. |
| 2007/0292518 | A1 | 12/2007 | Ludwig |
| 2007/0298257 | A1 | 12/2007 | Ludwig et al. |
| 2008/0051335 | A1 | 2/2008 | Kleiner et al. |
| 2008/0276935 | A1 * | 11/2008 | Wang ..................... 128/203.15 |
| 2008/0317813 | A1 | 12/2008 | Craig et al. |
| 2009/0324671 | A1 | 12/2009 | Ngo et al. |

(Continued)

OTHER PUBLICATIONS

U.S. Appl No. 11/015,943, filed Dec. 17, 2004, Pacetti et al.

(Continued)

*Primary Examiner* — Suzanne Ziska
(74) *Attorney, Agent, or Firm* — Squire Patton Boggs (US) LLP

(57) ABSTRACT

The current invention relates to methods of forming a coating that involves the in-situ formation of drug microspheres. The coating may be applied to a medical device, such as a catheter balloon or a stent. Coated devices and methods of treatment therewith are also encompassed within the embodiments of the present invention.

41 Claims, 5 Drawing Sheets

(56) References Cited

U.S. PATENT DOCUMENTS

| | | | |
|---|---|---|---|
| 2010/0209472 A1* | 8/2010 | Wang | 424/423 |
| 2010/0233236 A1 | 9/2010 | Zhao | |
| 2011/0129514 A1 | 6/2011 | Hossainy et al. | |
| 2011/0130829 A1* | 6/2011 | Clarke et al. | 623/1.42 |
| 2011/0137243 A1 | 6/2011 | Hossainy et al. | |
| 2011/0144578 A1* | 6/2011 | Pacetti et al. | 604/96.01 |

OTHER PUBLICATIONS

U.S. Appl No. 11/899,740, filed Sep. 6, 2007, Hossainy et al.
*90Plus Particle Size Analyzer* Brookhaven Instruments Corp. downloaded from www.bic.com/90Plus.html., Mar. 4, 2008, 6 pgs.
*Available Particle Characterization Technologies*, downloaded from www.malvern.com/LabEng/support/technologies.htm., Mar. 5, 2008, 3 pgs.
Design of Biopharmaceutical Properties through Prodrugs and Analogs, book, E. Roche Editor, 4 pgs. (1977).
*Laser Light Scattering*, downloaded from www.ap-lab.com/light_scattering.htm, Mar. 5, 2008, 8 pgs.
Microemulsion characterization using dynamic light scattering, Zetasizer Nano application note, downloaded from www.malvern.co.uk, 3 pgs. no date.
*Pigment Milling and Monitoring Particle Size Using Dynamic Light Scattering Techniques from Malvern Instruments*, downloaded from www.azom.com/details.asp!ArticleID=2724, Apr. 10, 2008, 5 pgs.
*Taking the "suspense" out of Nanosuspension Specifications*, downloaded from www.pharmtech.findpharma.com/pharmtech/content/printContentPopup.jsp, Apr. 9, 2008, 3 pgs.
*Toner size and shape characterization using FPIA-2100*, FPIA-2100 application note, downloaded from www.malvern.co.uk, 5 pgs. no date.
*When Particle Size is Importan*, Brookahven Instruments corp. downloaded from www.bic.com/Particle_sizers_overview_.html, Mar. 5, 2008, 1 pg.
Berkland et al., *Controlling surface namo-structure using flow-limited field-injection electrostatic spraying (FFESS) of poly(D, L-lactide-co-glycolide)*, Biomaterials 25, pp. 5649-5658 (2004).
Berkland et al., *Fabrication of PLG microspheres with precisely controlled and monodisperse size distribution*, J. of Controlled Release 73, pp. 59-74. (2001).
Berkland et al., *Precise control of PLG microsphere size provides enhanced control of drug release rate*, J. of Controlled Release 82, pp. 137-147 (2002).
Berkland et al., *Precision Polymer Microparticles for Controlled-Released Drug Delivery*, Am. Chem. Soc. pp. 197-213 (2004).
Bin Choy et al., *Uniform Biodegradable Hydrogel Microspheres Fabricated by a Surfactant-Free Electric-Field-Assisted Method*, Macromol. Biosci. vol. 7, pp. 423-428 (2007).
Chandrasekar et al., *Coronary Artery Endothelial Protection After Local Delivery of 17β-Estradiol During Balloon Angioplasty in a Porcine Model: A Potential New Pharmacologic Approach to Improve Endothelial Function*, J. of Am. College of Cardiology, vol. 38, No. 5, pp. 1570-1576 (2001).
Costa et al., Effect of uniform sized polymeric microspheres prepared by membrane emulsification technique on controlled release of anthracycline anti-cancer drugs, Desalination vol. 200, issues 1-3, pp. 498-500 (2006).
De Lezo et al., *Intracoronary Ultrasound Assessment of Directional Coronary Atherectomy: Immediate and Follow-Up Findings*, JACC vol. 21, No. 2, pp. 298-307 (1993).
Dimethylformamide Technical Data Sheet 3 pgs. (2004).
Dubey et al., *Factorial Effect of Process Parameters on Pharmaceutical Characteristics & Stability Study of PLGA Microspheres Containing Water-Soluble Drug*, downloaded from www.drugdeliverytech.com/cgi-bin/articles.cgi?idArticle=229, Apr. 9, 2008, 13 pgs.
Finsy et al., *Particle Sizing by Photon Correlation Spectroscopy. Part II: Average values*, Particle and particle Systems Characterization vol. 8, issue 1-4, pp. 187-193, Abstract 1 pg. (2004).

Hanus et al., *Conversion of intensity-averaged photon correlation spectroscopy measurements to number-averaged particle size distributions. 1. Theoretical development*, Langmuir vol. 15, No. 9, Abstract 1 pg. (1999).
Harper *Drug Latentiation*, Progress in Drug Research vol. 4, pp. 221-256 (1962).
Hua Ai et al., *Biomedical applications of electrostatic layer-by-layer nano-assembly of polymers, enzymes, and nanoparticles*, Cell Biochem. and Biophysics, vol. 39, No. 1, Abstract 1 pg. (2003).
Kim et al., *Drug Delivery, Contolled-release*, Office of Technology Management Univ. of Ill., 2 pgs. (2005-2006).
Kippax, *Measuring particle size using modern laser diffraction techniques*, downloaded from www.analytica-world.com/articles/e/, Mar. 5, 2008, 4 pgs.
Kosvintsev et al., *Liquid-Liquid Membrane Dispersion in a Stirred Cell with and without Controlled Shear*, Ind. Eng. Chem. Res. 44, pp. 9323-9330 Abstract only, 1 pg. (2005).
Lee et al., *In-vivo biocompatibility evaluation of stents coated with a new biodegradable elastomeric and functional polymer*, Coron. Artery. Dis., 13(4), pp. 237-241 (2002).
Martin et al., *Enhancing the biological activity of immobilized osteopontin using a type-1 collagen affinity coating*, J. Biomed. Mater. Res. 70A, pp. 10-19 (2004).
Micropore Technologies *emulsions-particles-filtration*, Abstract, 1 pg. downloaded from www.micropore.co.UK, Mar. 19, 2008.
Moreno et al., *Macrophage Infiltration Predicts Restenosis After Coronary Intervention in Patients with Unstable Angina*, Circulation, vol. 94, No. 12, pp. 3098-3102 (1996).
Nakashima et al., *Particle control of emulsion by membrane emulsification and its applications*, Advanced Drug Del. Rev. 45 pp. 47-56 (2000).
Oikawa et al., *Mechanisms of Acute Gain and Late Lumen Loss After Atherectomy in Different Preintervention Arterial Remodeling Patterns*, The Am. J. of Cardilogy, vol. 89, pp. 505-510 (2002).
Scheller et al., *Paclitaxel Ballon Coating, a Novel Method for Prevention and Therapy of Restenosis*, Circulation, 110; pp. 810-814 (2004).
Scully et al., *Effect of a heparan sulphate with high affinity for antithrombin III upon inactivation of thrombin and coagulaton Factor Xa*, Biochem J. 262, pp. 651-658 (1989).
Serruys et al., *A Randomized Comparison of the Value of Additional Stenting After Optimal Balloon Angioplasty for Long Coronary Lesions*, J. of Am. College of Cardiology vol. 39, No. 3, pp. 393-399 (2002).
Sinkula et al., *Rationale for Design of Biologically Reversible Drug Derivatives: Prodrugs*, J. of Pharmac. Science vol. 64, No. 2, pp. 181-210 (1975).
Spagnuolo et al., *Gas1 as induced by VE-cadherin and vascular endothelial growth factor and inhibits endothelial cell apoptosis*, Blood vol. 103, No. 8, pp. 3005-3012 (2004).
Stella et al., *Prodrugs Do They Have Advantages in Clinical Practice?*, Drugs 29, pp. 455-473 (1985).
The knowledge database about lactose, Particle Size Distribution D10, D50 and D90, downloaded from www.lactose.com/particle_size/d10_d50_d90.html, Apr. 9, 2008, 2 pgs.
US Pharmacopeia test method <788> Particulate matter in Injections, 6 pgs. downloaded from www.usp.org. Jun. 9, 2011.
Virmani et al., *Lessons From Sudden Coronary Death a Comprehensive Morphological Classification Scheme for Atherosclerotic Lesions*, Arterioscler Thromb Vasc Biol. pp. 1262-1275 (2000).
Völkel et al., *Targeting of immunoliposomes to endothelial cells using a single-chain Fv fragment directed against human endoglin (CD105)*, Biochemica et Biophysica Acta, vol. 1663, pp. 158-166 (2004).
"Vapor Pressure of Pure Substances", Perry's Chemical Engineers' Handbook, sixth ed. McGraw-Hill Book Co. 1984, pp. 3-45, attached 3 pgs.
Acetone, Material Safety Data Sheet, downloaded: www.fscimage.fishersci.com/msds/00140.htm, Aug. 29, 2012, 7 pgs.
Acetone, NST, downloaded: www.webbook.nist.gov./cgi/cbook.cgi?ID=C67641&Mask=200, Aug. 29, 2012, 4 pgs.
Acetone, Wikipedia, downloaded: www.wikipedia.org/wiki/Acetone, Aug. 29, 2012, 1 pg.

(56) References Cited

OTHER PUBLICATIONS

Chemical Properties, downloaded: www.students.chem.tue.nl/ana21/Safety/Chemical%20LProperties.htm, Aug. 29, 2012, 2 pgs.

Du et al., "Synthesis and evaluation of water-soluble docetaxel prodrugs-docetaxel esters of malic acid", Bioorganic & Medicinal Chemistry 15 pp. 6323-6330 (2007).

Everolimus (RAD0001), product citations, Selleckchem.com, downloaded: www.selleckchem.com/products/Everolimus(RAD001).html, Aug. 29, 2012, 3 pgs.

Gandhi et al., "Solubility and Crystal Size of Sirolimus in Different Organic Solvents", J. Chem. Eng. Data 55, pp. 5050-5054 (2010).

Liggins et al., "Solid-State Characterization of Paclitaxel", J. of Pharmaceutical Sciences vol. 86, No. 12, pp. 1458-1463 (1997).

Methanol, Material Safety Data Sheet, downloaded: www.fscimage.fishersci.com/msds/14280.htm, Aug. 29, 2012, 7 pgs.

Methanol, Wikipedia, downloaded: www.en.wikipedia.org/wiki/Methanol, Aug. 29, 2012, 1 pg.

Min-Soo Kim et al., "Enhanced bioavailability of sirolimus via preparation of solid dispersion nanoparticles using a supercritical antisolvent process", Int. J. of Nanomedicine 6, pp. 2997-3009 (2011).

Molecular weight of Acetone, downloaded: www.convertunits.com/molarmass/Acetone, Aug. 29, 2012, 1 pg.

Niethammer et al., "Synthesis and Preclinical Characterization of a Paclitaxel Prodrug with Improved Antitumor Activity and Water Solubility", Bioconjugate Chem. 12, pp. 414-420 (2001).

Phenomenex miscibility table—downloaded: http://www.erowid.org/archive//rhodium/pdf/solvent.miscibility.pdf, Aug. 29, 2012, 1 pg.

RAD001 BHT/DS 01, Safety Data Sheet, Novartis, 4 pgs. (2000).

Rapamycin, product data sheet, (BIA-r1183) bioaustralis fine chemicals, www.bioaustralis.com, Aug. 29, 2012, 1 pg.

Simamora et al., "Solubilization of rapamycin", Int. J. of Pharmaceutics 213, pp. 25-29 (2001).

Solubility of alcohols (eg. ethanol), SolubilityOfThings, downloaded: www.solubilityofthings.com/water/alcohols, Aug. 29, 2012, 1 pg.

Taxotere® Prodrug, Aphios Corporation, downloaded: www.aphios.com/pipeline/TaxotereProdrug.htm, Aug. 29, 2012, 2 pgs.

\* cited by examiner

DRUG COATED BALLOON WITH IN-SITU FORMED DRUG CONTAINING MICROSPHERES

FIELD

This invention relates to chemistry, physiology, material science and drug delivery.

BACKGROUND

Until the mid-1980s, the accepted treatment for atherosclerosis, i.e., narrowing of the coronary artery(ies) was coronary by-pass surgery. While effective and having evolved to a relatively high degree of safety for such an invasive procedure, by-pass surgery still involves serious potential complications and in the best of cases an extended recovery period.

With the advent of percutaneous transluminal coronary angioplasty (PTCA) in 1977, the scene changed dramatically. Using catheter techniques originally developed for heart exploration, inflatable balloons were employed to re-open occluded regions in arteries. The procedure was relatively non-invasive, took a very short time compared to by-pass surgery and the recovery time was minimal. However, PTCA brought with it another problem, elastic recoil of the stretched arterial wall which could undo much of what was accomplished and, in addition, creation of the iatrogenic disease known as restenosis, the re-clogging of the treated artery. Another problem associated with PTCA is the formation of intimal flaps or torn arterial linings which can collapse and occlude the blood conduit after the balloon is deflated.

To reduce the partial or total occlusion of the artery by the collapse of the arterial lining and to reduce the chance of thrombosis or restenosis, a stent may be implanted in the artery to keep the artery open. Drug delivery stents have reduced the incidence of in-stent restenosis, which has plagued interventional cardiology for more than a decade.

An alternative to a drug-delivery stent is a drug coated balloon (DCB). A coating containing a drug is formed on the exterior of a balloon. When the balloon is inflated, and the balloon walls contact the vessel walls, the drug is released. The challenges facing the preparation of such coated expandable devices include designing a coating that remains substantially intact during expansion which then delivers the drug to the vessel walls during the procedure. In practice, the majority of the drug is released from the surface of the balloon during its inflation, which may be a few seconds to a few minutes. The challenges in designing such a balloon coating differ from those of designing a coating for a stent or other implantable device which is designed to release the drug over a time period of days, weeks, or even months.

If the coating flakes off a DCB, the coating may present an embolic hazard. This is particularly a concern since many of the drugs that may be useful for delivery via DCB are hydrophobic and dissolve slowly in the bloodstream. Particles or fragments of a coating released from the DCB could produce an embolism if the particle or fragment is larger than the diameter of the vessel. Although drugs will eventually dissolve in vivo, a particle of a hydrophobic drug could potentially present an embolic hazard because the in vivo dissolution or disintegration is slow.

The current invention is directed to methods of coating expandable medical devices, such as catheter balloons, and to the devices themselves that have been so coated. The present invention addresses potential embolic hazards with hydrophobic drugs.

SUMMARY

The current invention is directed to methods of coating medical devices, particularly expandable medical devices, and the devices themselves that include such coatings.

Thus, in one aspect of the present invention is a method for coating a medical device. The method includes forming a homogeneous coating solution by dissolving a hydrophobic drug having a solubility in phosphate buffered saline of about 1 mg/ml or less than 1 mg/ml in a coating solvent including one or more first solvents in which the drug has a solubility of not more than 2000 mg/liter and one or more second solvents in which the drug has a solubility of not less than 10,000 mg/liter, disposing the coating solution over a surface of the medical device; removing the one or more second solvents at a temperature and pressure selected such that the drug precipitates from the remaining coating solution as particles of a volume weighted average size of 30 microns or less; and removing the remaining coating solvent. The one or more second solvents is/are more volatile than the one or more first solvents by at least a factor of 2.

In an aspect of the present invention, the medical device is an expandable medical device.

In an aspect of the present invention, the wt/wt ratio of drug to the one or more first solvents is about equal to or greater than 1/99 and about equal to or less than 50/50.

In an aspect of the present invention, the coating solution comprises a suspending agent/surfactant.

In an aspect of the present invention, the coating solution comprises a binder.

In an aspect of the present invention, the one or more first solvents have a vapor pressure measured at 20° C. of at least 0.5 torr.

In an aspect of the present invention, the one or more second solvents have a vapor pressure at 20° C. of not more than 450 torr.

In an aspect of the present invention, the one or more second solvents is/are more volatile than the one or more first solvents by at least a factor of 50.

In an aspect of the present invention, the one or more second solvents is/are more volatile than the one or more first solvents by at least a factor of 750.

In an aspect of the present invention, the one or more second solvent(s) is/are selected from the group consisting of methanol, ethanol, isopropanol, 1-propanol, acetone, 2-butanone, diethyl ether, tetrahydrofuran, methyl acetate and ethyl acetate.

In an aspect of the present invention, disposing the coating solution over the substrate is accomplished by spraying, rolling, pipetting, brushing, ink-jet application, silk screening, direct fluid application, or dip coating.

In an aspect of the present invention, the method further includes applying a gas stream of air, nitrogen, argon or other inert gas to the medical device.

In an aspect of the present invention, the application of the gas stream occurs simultaneously with disposing the coating solution over the substrate.

In an aspect of the present invention, the application of the gas stream occurs after disposing the coating solution over the substrate.

In another embodiment of the present invention is a medical device including a coating applied using any of the methods described herein.

In another embodiment of the present invention is a medical device including a coating including a particulate hydrophobic drug wherein upon expansion of the device, not more than 40% of particles of the drug cast off from the coating have a diameter of greater than 30 μm based upon the volume average distribution.

In an aspect of the present invention, the device is a balloon catheter.

In an aspect of the present invention, not more than 20% of the drug particles have a diameter of greater than 30 μm.

In an aspect of the present invention, not more than 10% of the particles have a diameter of greater than 30 μm.

In an aspect of the present invention, the coating further comprises a suspending agent/surfactant.

In an aspect of the present invention, the coating further comprises a binder.

In another aspect of the present invention, the drug is selected from the group consisting of zotarolimus, everolimus, sirolimus, biolimus A9, deforolimus, AP23572, tacrolimus, temsirolimus, pimecrolimus, novolimus, myolimus, paclitaxel, protaxel, and derivatives and combinations thereof.

In another aspect of the present invention, the suspending agent/surfactant is selected from the group consisting of carboxymethyl cellulose, sodium carboxymethyl cellulose, diethanolamine carboxymethyl cellulose, carboxymethyl cellulose derivatives, polysorbates, TWEEN™ 20 (polysorbate 20), TWEEN™ 80 (polysorbate 80), poly(vinyl alcohol), lecithin, gelatin, sucrose, 1,2-distearoyl-sn-glycero-3-phospho-ethanolamine-N-[methoxy(polyethylene glycol)-2000](ammonium salt) (PEG-PE), phosphatidyl choline, phospholipids, pegylated phospholipids, TWEEN™ 60 (polysorbate 60), vitamin E TPGS, PLURONIC® 68 which is a poly(ethylene oxide)-poly(propylene oxide) block copolymers, poly(ethylene oxide)-poly(propylene oxide) block copolymers, poloxamers 188 and 407, ascorbyl palmitate, CREMOPHOR EL™, fatty alcohols, fatty esters, tocopherols, phospholipids and combinations thereof.

In an aspect of the present invention, the binder is selected from the group consisting of poly(ethylene glycol), poly(2-hydroxyethyl methacrylate), poly(hydroxypropyl methacrylamide), poly(vinyl alcohol), chitosan, sodium alginate, hydroethyl cellulose, hydroxypropyl cellulose, methyl cellulose, ethyl cellulose, dextran, and poly(vinyl pyrrolidone), and combinations thereof.

In an aspect of the present invention, the suspending agent and/or surfactant is diethanolamine-carboxymethyl cellulose (DEA-CMC, ratio DEA/CMC approximately 25/75 (w/w)).

In an aspect of the present invention, the drug is zotarolimus or everolimus, both immunosuppressive macrolide antibiotics.

In an aspect of the present invention, water or deionized water is the first solvent, and methanol is the second solvent.

In an aspect of the present invention, the coating thickness is between 0.1 to 30 microns.

In an aspect of the present invention, the drug loading is between 10 to 1000 μg/cm$^2$.

In an aspect of the present invention, the drug loading is between 50 to 720 μg/cm$^2$.

Embodiments of the present invention encompass methods and devices including any one or more of the above aspects of the present invention.

Embodiments of the present invention encompass methods of treatment with any coated device described herein.

In an aspect of the present invention, the method of treatment is the treatment of conditions in the peripheral vasculature and specifically the SFA.

DETAILED DESCRIPTION

DISCUSSION

Figure 1:
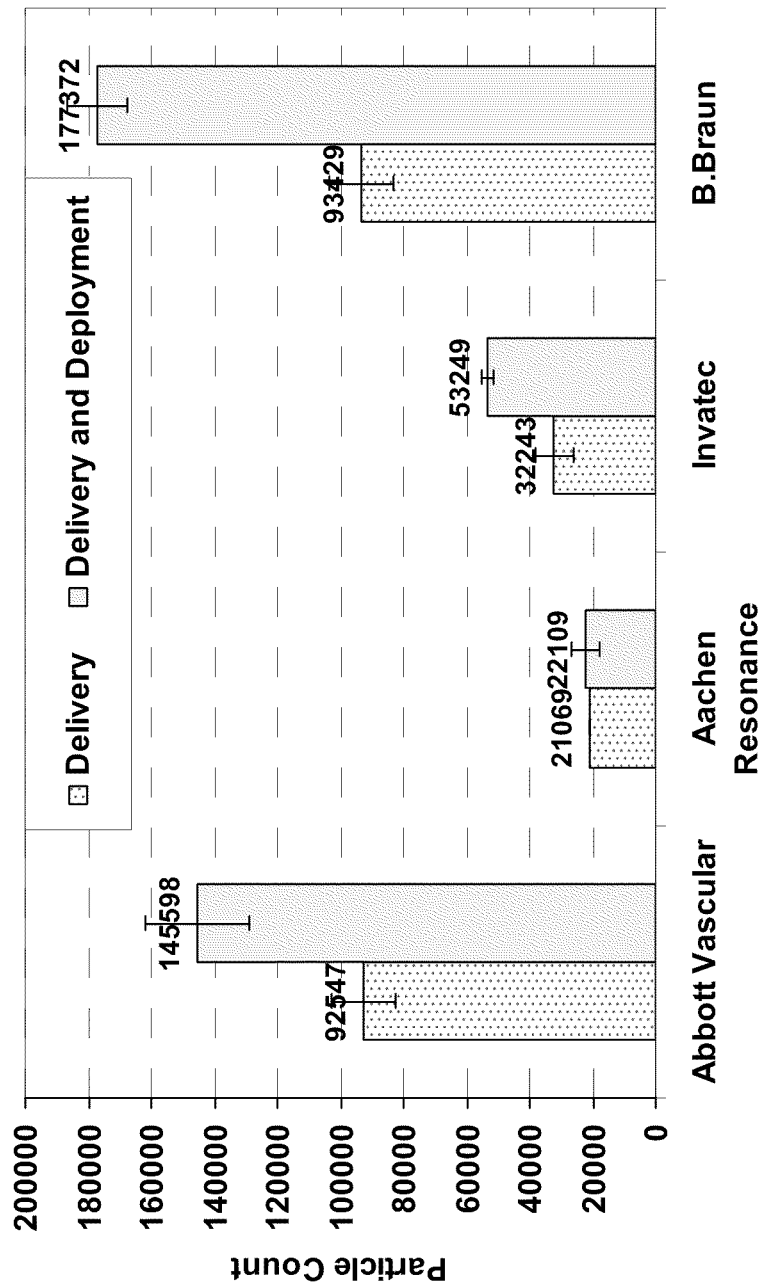
FIG. 1 is a histogram of the number of particles in the 10-25 micron range released from a number of commercially available coronary drug coated balloons.

Use of the singular herein includes the plural and vice versa unless expressly stated to be otherwise. That is, "a" and "the" refer to one or more of whatever the word modifies. For example, "a drug" may refer to one drug, two drugs, etc. Likewise, "the balloon" may refer to one, two or more balloons and "the polymer" may mean one polymer or a plurality of polymers. By the same token, words such as, without limitation, "balloons" and "polymers" would refer to one balloon or polymer as well as to a plurality of balloons or polymers unless it is expressly stated or obvious from the context that such is not intended.

As used herein, words of approximation such as, without limitation, "about," "substantially," "essentially," and "approximately" mean that the word or phrase modified by the term need not be exactly that which is written but may vary from that written description to some extent. The extent to which the description may vary will depend on how great a change can be instituted and have one of ordinary skill in the art recognize the modified version as still having the properties, characteristics and capabilities of the modified word or phrase. In general, but with the preceding discussion in mind, a numerical value herein that is modified by a word of approximation may vary from the stated value by ±15%, unless expressly stated otherwise.

As used herein, any ranges presented are inclusive of the end-points. For example, "a temperature between 10° C. and 30° C." or "a temperature from 10° C. to 30° C." includes 10° C. and 30° C., as well as any temperature in between.

As used herein, the use of "preferred," "preferably," or "more preferred," and the like to modify an aspect of the invention refers to preferences as they existed at the time of filing of the patent application.

As used herein, "optional" means that the element modified by the term may or may not be present.

As used herein, an "implantable medical device" refers to any type of appliance that is totally or partly introduced, surgically or medically, into a patient's body or by medical intervention into a natural orifice, and which is intended to remain there after the procedure. The duration of implantation may be essentially permanent, i.e., intended to remain in place for the remaining lifespan of the patient; until the device biodegrades; or until it is physically removed. Examples of implantable medical devices include, without limitation, implantable cardiac pacemakers and defibrillators; leads and electrodes for the preceding; implantable organ stimulators such as nerve, bladder, sphincter and diaphragm stimulators; cochlear implants; prostheses, vascular grafts, self-expandable stents, balloon-expandable stents, stent-grafts, grafts, artificial heart valves, foramen ovale closure devices, cerebrospinal fluid shunts, and intrauterine devices.

One type of implantable medical device is a stent. Stents are implantable medical devices that are generally cylindrically shaped and function to hold open, and sometimes expand, a segment of a blood vessel or other vessel in a patient's body when the vessel is narrowed or closed due to diseases or disorders including, without limitation, tumors (m, for example, bile ducts, the esophagus, the trachea/bronchi, etc.), benign pancreatic disease, coronary artery disease, carotid artery disease and peripheral arterial disease. A stent can be used in, without limitation, neuro, carotid, coronary, pulmonary, aorta, renal, biliary, iliac, femoral and popliteal, as well as other peripheral, vasculatures, and in other bodily lumens such as the urethra or bile duct. A stent can be used in the treatment or prevention of disorders such as, without limitation, atherosclerosis, vulnerable plaque, thrombosis, restenosis, hemorrhage, vascular dissection or perforation, vascular aneurysm, chronic total occlusion, claudication, anastomotic proliferation, bile duct obstruction and ureter obstruction.

Another type of medical device is a vascular catheter. A vascular catheter is a thin, flexible tube with a manipulating means at one end, referred to as the proximal end, which remains outside the patient's body, and an operative device at or near the other end, called the distal end, which is inserted into the patient's artery or vein. The catheter may be introduced into a patient's vasculature at a point remote from the target site, e.g., into the femoral artery of the leg where the target is in the vicinity of the heart. The catheter is steered, assisted by a guide wire than extends through a lumen, that is a passageway or cavity, in the flexible tube, to the target site whereupon the guide wire is withdrawn at which time the lumen may be used for the introduction of fluids, often containing drugs, to the target site. A catheter may also be used to deliver a stent or may be used to deliver a balloon used in angioplasty.

As used herein, a "balloon" refers to the well-known in the art device, usually associated with a vascular catheter, that comprises a relatively thin, flexible material, forming a tubular membrane, that when positioned at a particular location in a patient's vessel can be expanded or inflated to an outside diameter that is essentially the same as the inside or luminal diameter of the vessel in which it is placed. In addition to diameter, a balloon has other dimensions suitable for the vessel in which it is to be expanded. Balloons may be inflated, without limitation, using a liquid medium such as water or normal saline solution, that is, saline that is essentially isotonic with blood.

A "balloon catheter" refers to medical device which is system of a catheter with a balloon at the end of the catheter.

A balloon, a catheter, and a stent differ. Stents are typically delivered to a treatment site by being compressed or crimped onto a catheter or onto a catheter balloon, and then delivered through narrow vessels to a treatment site where the stent is deployed. Deployment involves expanding the stent to a larger diameter, typically to the diameter of the vessel, once it is at the treatment site. Stents can be self-expanding or balloon expandable. The expanded stent is capable of supporting a bodily lumen for an extended period of time. In contrast, a balloon has a wall thickness that is so thin that the tubular membrane cannot support a load at a given diameter unless inflated with a fluid, such as a liquid or gas. Furthermore, a balloon is a transitory device that is inserted in the patient's body for only a limited time for the purpose of performing a specific procedure or function. Unlike a stent, dilatation balloons are not permanently implanted within the body.

As used herein, a material that is described as a layer or a film (e.g., a coating) "disposed over" an indicated substrate refers to, e.g., a coating of the material deposited directly or indirectly over at least a portion of the surface of the substrate. Direct depositing means that the coating layer is applied directly to the surface of the substrate. Indirect depositing means that the coating layer is applied to an intervening layer that has been deposited directly or indirectly over the substrate. A coating layer is supported by a surface of the substrate, whether the coating layer is deposited directly, or indirectly, onto the surface of the substrate. The terms "layer", and "coating layer" will be used interchangeably and refer to a layer, film, or coating layer as described above in this paragraph. A coating may include multiple coating layers or may be only one layer. Each coating layer may be formed by multiple applications of coating material. As used herein, unless the context indicates otherwise or it is expressly stated otherwise, a coating layer is not chemically or covalently bound to the substrate, or a preexisting coating layer, onto which it has been deposited.

As used herein, "therapeutic agent," "drug" or "active agent," which will be used interchangeably, refers to any substance that, when administered in a therapeutically effective amount to a patient (an animal, but typically, a human being) suffering from a disease or condition, has a therapeutic beneficial effect on the health and well-being of the patient. A therapeutic beneficial effect on the health and well-being of a patient includes, but is not limited to: (1) curing the disease or condition; (2) slowing the progress of the disease or condition; (3) causing the disease or condition to retrogress; or, (4) alleviating one or more symptoms of the disease or condition.

As used herein, a drug also includes any substance that when administered to a patient, known or suspected of being particularly susceptible to a disease, in a prophylactically effective amount, has a prophylactic beneficial effect on the health and well-being of the patient. A prophylactic beneficial effect on the health and well-being of a patient includes, but is not limited to: (1) preventing or delaying on-set of the disease or condition in the first place; (2) maintaining a disease or condition at a retrogressed level once such level has been achieved by a therapeutically effective amount of a substance, which may be the same as or different from the substance used in a prophylactically effective amount; or, (3) preventing or delaying recurrence of the disease or condition after a course of treatment with a therapeutically effective amount of a substance, which may be the same as or different from the substance used in a prophylactically effective amount, has concluded.

As used herein, "therapeutic agent," "drug" or "active agent" also refers to pharmaceutically acceptable, pharmacologically active derivatives of those drugs specifically mentioned herein, including, but not limited to, salts, esters, amides, prodrugs, active metabolites, analogs, and the like, and to non-toxic substances useful as diagnostic agents.

As used herein, a "polymer" refers to a molecule comprised of, actually or conceptually, repeating "constitutional units." The constitutional units derive from the reaction of monomers. As a non-limiting example, ethylene ($CH_2=CH_2$) is a monomer that can be polymerized to form polyethylene, $CH_3CH_2(CH_2CH_2)_nCH_2CH_3$ (where n is an integer), wherein the constitutional unit is —$CH_2CH_2$—, ethylene having lost the double bond as the result of the polymerization reaction. The constitutional units themselves can be the product of the reactions of other compounds. A polymer may be derived from the polymerization of several different types of monomers or may be formed of several different types of constitutional units. Such polymers are referred to as "copolymers." Those skilled in the art, given a particular polymer, will readily recognize the constitutional units of that polymer and will equally readily recognize the structure of the monomer from which the constitutional units derive. As used herein, the term polymer refers to a molecule comprising more than 20 constitutional units.

Polymers may be straight or branched chain, star-like or dendritic, or one polymer may be attached (grafted) onto another. Polymers may have a random disposition of constitutional units along the chain, the constitutional units may be present as discrete blocks, or constitutional units may be so disposed as to form gradients of concentration along the polymer chain. In other words, the polymers used in this invention may be regular alternating polymers, random alternating polymers, regular block polymers, random block polymers or purely random polymers unless expressly noted otherwise. Polymers may be cross-linked to form a network.

As used herein, a molecule which has a chain length of 20 or fewer constitutional units is referred to as an "oligomer."

As used herein, "binder" is a substance that assists in holding other substances together and/or assists in holding the other substances onto a substrate. A binder does not function through covalent bonding to the other substances, but through colloidal forces, van der Waals forces, ionic interactions, dipole-dipole interactions, dipole-induced dipole interactions, hydrogen-bonding, or other interactions not involving the formation of a covalent bond. The use of the word "binder" herein is consistent with the use in the field of pharmaceutical formulations.

As used herein, "solvent" is defined as a substance capable of dissolving one or more other substances or capable of at least partially dissolving the other substance(s) to form a uniformly dispersed solution at the molecular- or ion-size level at a selected temperature and pressure. A solvent can refer to one chemical compound, or a mixture of chemical compounds. A solvent can be a fluid. A substance may be a solvent even though the amount of another substance that it can dissolve is very small.

As used herein, a suspending agent is a substance which keeps another substance dispersed or suspended in a fluid in which it is insoluble, or in which it is present above its solubility limit for that fluid.

One type of suspending agent is a surfactant. Surfactants are typically amphiphilic molecules. Amphiphilic molecules have two distinct components, differing in their affinity for a solute, most particularly water. The part of the molecule that has an affinity for non-polar solutes such as hydrocarbons is said to be hydrophobic. The part of the molecule that has an affinity for water is said to be hydrophilic. When amphiphilic molecules are placed in water, the hydrophilic part or moiety seeks to interact with the water while the hydrophobic part or moiety seeks to avoid the water. To accomplish this, the hydrophilic moiety remains in the water while the hydrophobic moiety is held above the surface of the water in the air or in a non-polar, non-miscible liquid floating on the water, or alternatively, the hydrophobic moiety is in droplets of the non-polar, non-miscible liquid dispersed in the water. The presence of this layer of molecules at the water's surface disrupts the cohesive energy at the surface and lowers surface tension. Amphiphilic molecules that have this effect are known as "surfactants."

Surfactants are capable of forming "micelles." A micelle is a spherical colloidal particle spontaneously formed by many amphiphilic molecules in an aqueous medium when the Critical Micelle Concentration (CMC) is exceeded. Only so many surfactant molecules can align as just described at the water/air or water/hydrocarbon interface or dissolve unimolecularly in the solution. When the interface becomes so crowded with surfactant molecules that no more can fit in, and when the solution becomes saturated, i.e., when the CMC is reached, any remaining surfactant molecules will form into spheres with the hydrophilic ends of the molecules facing out, that is, in contact with the water, and with the hydrophobic ends facing toward the center of the of the sphere forming the micelle core or center.

As used herein, "phosphate buffer solution" refers to an aqueous solution of phosphate salts. Typically, these are orthophosphate salts of sodium or potassium. The buffer solution is at a pH 7.4 and may contain saline (0.9% by weight NaCl) to form phosphate buffered saline (PBS).

As used herein, "particle" is a piece of matter held together by physical bonding of molecules, an agglomeration of pieces of matter ("particles") held together by colloidal forces and/or surface forces, a piece of matter which is held together by chemical bonds such as a cross-linked polymer network, a piece of matter formed by ionic interactions, or a piece of matter held together by any combination of agglomeration, surface forces, colloidal forces, ionic interactions, and chemical bonds. For the purposes of this disclosure, a particle will be defined as ranging in size from less than a one tenth of a nanometer to several centimeters in size.

The polydispersity of a plurality of particles represents the distribution of sizes, usually expressed as particle diameters, within a plurality of particles. The average diameter can be a number average diameter, where the number average diameter=$\Sigma_i\, d_i n_i / \Sigma_i n_i$ where $n_i$ represents the number of particles with a diameter represented by $d_i$. Usually approximations are made and the distribution of particles by diameters is represented as a histogram, or in other words the particles are divided into smaller groups encompassing a smaller range of diameters and each of these groups is assigned a diameter near the center of that range. The surface area average diameter is determined by $(\Sigma_i\, f_i d_i^2)^{1/2}$, and the volume or mass average diameter is determined by $(\Sigma_i f_i d_i^3)^{1/3}$, where $f_i$ is $n_i/\Sigma_i\, n_i$. Thus, in the case of the surface area average, the weighting factor is the surface area represented by the class of particles of diameter $d_i$ while for the volume average diameter, the weighting factor is the volume represented by each class of particles of diameter $d_i$. Since the surface area increases with diameter squared and the volume increases with diameter cubed, the surface area average diameter is greater than the number average diameter. Likewise, the volume average diameter exceeds the surface area diameter. The mass or weight average diameter is the same as the volume average diameter if the density of all of the particles is the same. Similarly, distributions of particle sizes may be based on the number, surface area, or volume of the particles. As used herein, unless expressly stated otherwise or obvious from the context that another definition applies, any reference to the average diameter of a plurality of particles will refer to the volume average diameter.

The distribution of the particle sizes in a plurality may be represented by the standard deviation, which is a well-known statistical measurement. The standard deviation may be suitable for a narrow particle size distribution. Other measures of polydispersity include the d10 and d90 which refer to the diameters representing the threshold where 10% of the distribution falls below, and 90% of the distribution falls below, respectively. The average may be referred to as a d50. Thus for a number average, half or 50% of the number of particles have a diameter less than the d50. For a volume average diameter, the d50 represents the diameter where half the volume represented by the plurality is in particles having a diameter smaller than d50, or in other words, the intersection of the 50% line on a plot of the cumulative volume of the particles as a function of diameter.

Embodiments of the present invention are directed to methods of forming coatings, and particularly, coatings for medical devices, such as without limitation, a balloon of a balloon catheter, and the devices so coated. The design of drug coated balloons, that is the well-known balloon typically associated with a vascular catheter that have been coated with a drug or drug formulation, present several challenges. First the coating must remain intact, or substantially intact, during delivery and expansion. The majority of the drug must be delivered, that is released from the balloon surface, during the inflation which may be a few seconds to a few minutes. In addition, the drug coating must comply with standards for drug uniformity and drug content, and must be able to withstand sterilization. Another challenge is the presence of a relatively high drug loading for a DCB as compared to a drug delivery stent.

Due to the fact that most of the drug must be released quickly during the procedure, primarily during the inflation, a large portion of the drug being released is released into the systemic circulation as opposed to being absorbed into the tissue. Studies have shown that the highest uptake by the tissue from DCBs is approximately 15-17%. (Circulation 2004; 110: 810-814.)

The drug loadings are also higher for DCBs than for drug delivery stents that are designed to deliver drug over extended time periods such as weeks or months. As a non-limiting example, a 12 mm coronary drug eluting stent with everolimus in the coating has a drug loading of about 55 µg and a coatable surface area of about 0.56 cm$^2$, or approximately 100 µg/cm$^2$. In contrast, a typical drug coated balloon has a greater coated surface area than a stent and a loading approximately three times greater. For larger balloons, such as, without limitation, a 6×100 mm peripheral balloon, the total quantity of drug may be substantial, that is about 11 mg per balloon. Because a large percentage of the drug will be released systemically into the blood stream, as opposed to be absorbed into the tissue, systemic toxicity issues must be addressed.

Figure 2:
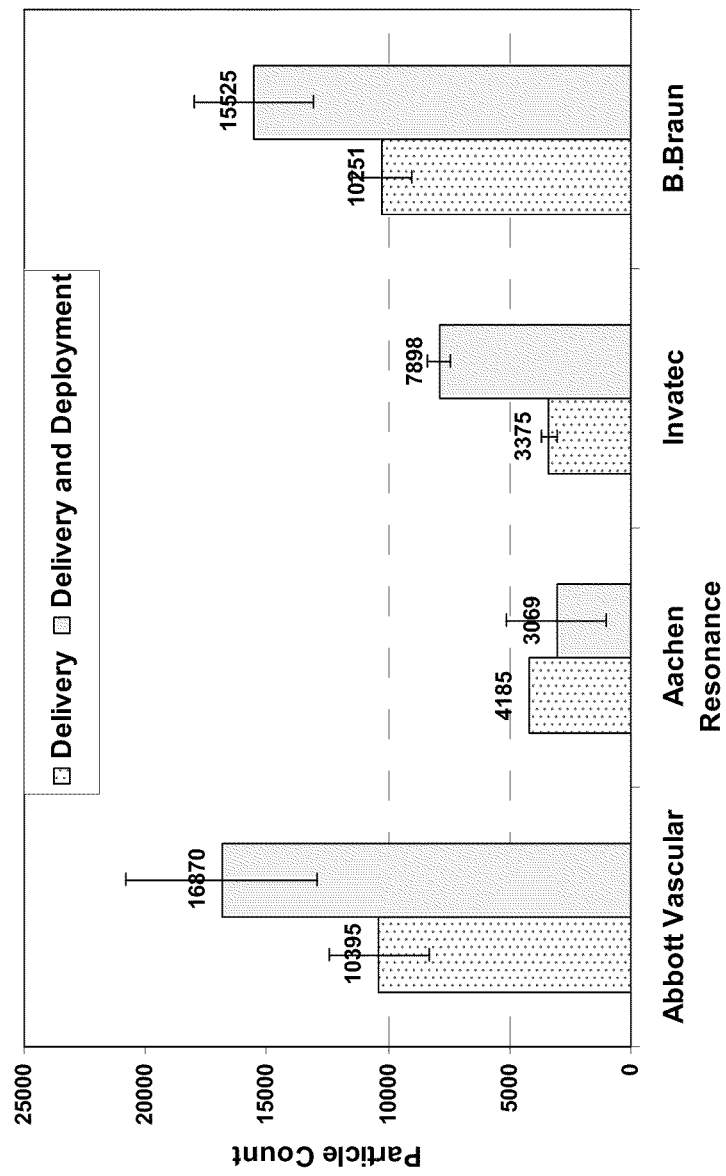
FIG. 2 is a histogram of the number of particles in the 25-50 micron range released from a number of commercially available coronary drug coated balloons.

An experiment, described in example 1 below, was performed on a number of currently marketed drug coated balloon products. Briefly, the drug coated balloons were "delivered," that is maneuvered to a "treatment site" in a model filled with PBS at 37° C. The DCBs were then "deployed," that is inflated to a nominal pressure after "delivery" to the "treatment site" in the model, held for 30 seconds, and then deflated and removed from the model. The number of "particles" shed from the DCB into the PBS solution before and after inflation was determined. FIGS. 1 and 2 provide the particle counts before and after balloon inflation. FIG. 1 provides the particle counts for particles in the 10-25 micron range, and FIG. 2 provides the particle counts for particles in the 25-50 micron range. As illustrated in FIGS. 1 and 2, the number of particles in the PBS is significant.

Although not directly applicable, the United States Pharmacopeia (USP) specifications for small volume injectable parenteral products, USP test method 788, were used as a basis for comparison. The USP provides specifications for the number of particles for injectable products of specified volumes. It is believed that specifications of this nature may be applied to DCBs as the DCBs present an analogous situation since the DCBs shed particles into the bloodstream. For particles greater than 10 microns, USP 788 specifies not more than 6000 particles for an injection volume of <100 ml, and for particles greater than 25 microns, USP 788 specifies not more than 600 particles for an injection volume of <100 ml. As the results in FIGS. 1 and 2 illustrate, the numbers of particles released from these drug coated balloons are far in excess of these specifications.

The particles released from these DCBs will all eventually dissolve. However, the time frame for dissolution or degradation is important. If the particles are of sufficient size to block an artery, a local ischemia, that is a cutting off of the blood supply and thus oxygen, may result. Ischemia lasting longer than 4 minutes may result in cell death and tissue damage. As a result, the size and composition of the particles that are cast off, i.e. "shed," from the drug coated balloon are a safety concern. Red blood cells are approximately 8 microns in diameter and thus the smallest blood vessels are at least about 10 microns in diameter. Therefore, particles that are less than 10 microns in diameter are generally considered non-embolic. Particles that dissolve quickly are also less likely to cause a local ischemia.

One manner of ensuring that the particles cast off by the drug coated balloon are of a size that is non-embolic is to formulate the drug as microspheres of an appropriate size. The drugs can be made into microspheres, optionally including other excipients, and then coated onto the balloon. This approach is potentially problematic for a number of reasons. First, there are additional steps to manufacture the microspheres. Second, if the microspheres are coated onto a balloon as a traditional coating layer, that is by suspension or dispersion in a fluid to form a composition which is applied to the surface of the balloon with removal of the fluid, the microspheres must be kept uniformly suspended or dispersed in the fluid. Over time, the microspheres may aggregate or flocculate, and/or may settle to the bottom of the container, potentially resulting in variations in drug content and uniformity. Third, the use of a dispersion of the microspheres in solution would not allow for filtration through a 0.2 µm or 0.45 µm filter which is regularly done to ensure removal of any opportunistic particulate contamination of the containers, materials, or fluid utilized.

The present invention is directed to methods which avoid many of these problems by forming the microspheres of drug in situ, and to the devices that are coated using such methods. It has unexpectedly been found that application of coating solution including a drug from an appropriate solution results in the in situ formation of microspheres of the appropriate size. The microspheres cast off from the coated balloon are individual microspheres or aggregates of microspheres. Embodiments of the present invention encompass methods including, but not limited to, forming a homogenous coating solution of a hydrophobic drug in a mixture of at least two solvents. One solvent is a good solvent for the drug, and one solvent is a poor solvent for the drug. The good solvent has a higher volatility than the poor solvent. The homogenous solution is disposed over a substrate, such as but not limited to the surface of balloon of a balloon catheter, and the drug is induced to precipitate and form microspheres in situ on the substrate surface. The coating solution may optionally include a suspending agent, and/or a binder. The result is a drug coated balloon in which the drug is present as microspheres, and for which a majority of the particles that are cast off have a diameter of less than or equal to 30 microns based on a volume distribution of particle sizes.

Although the discussion that follows will focus on the inflatable portion, that is the balloon, of a balloon catheter as the substrate for the application of the coating layer, other medical devices may also serve as substrates. Expandable medical devices are preferred substrates, but embodiments of the present invention are not limited to expandable medical devices. A stent is an example of another type of expandable medical device. A medical device specifically designed and intended solely for the localized delivery of a drug is within the scope of this invention.

Figure 3:
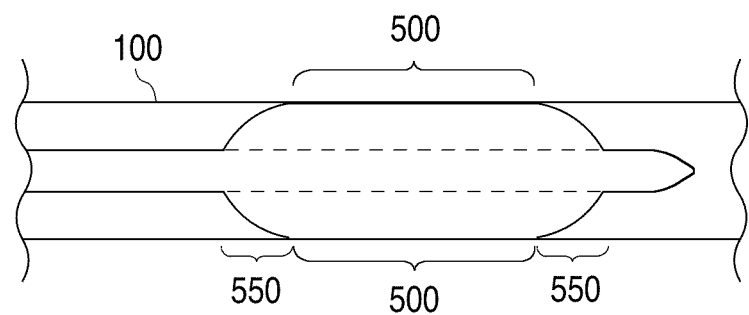
FIG. 3 is a schematic depiction of a typical balloon catheter inflated in a bodily lumen.
Figure 4:
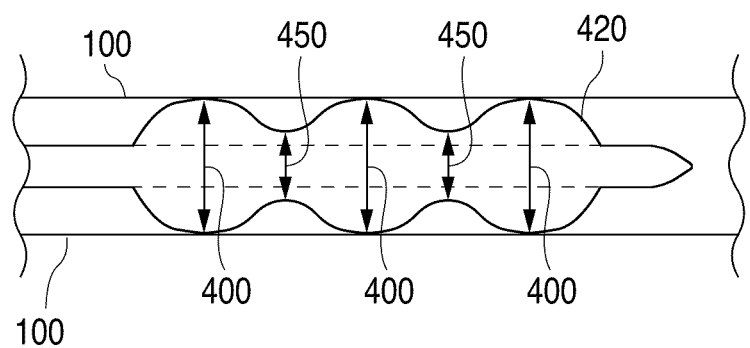
FIG. 4 is a schematic depiction of another type of balloon catheter inflated in a bodily lumen.

Although the discussion that follows focuses on a typical balloon catheter, a number of different types of balloon catheters may be used. For example, a balloon used with embodiments of this invention may have substantially a single diameter over its entire length such that the full length of the balloon 500 is in contact with the wall of the vessel 100, as shown in FIG. 3. The length 500 is referred to as the working length and encompasses the length in contact with the walls, but excludes the tapered ends 550 shown in FIG. 3. A balloon may also comprise two different outside diameters. An example is illustrated in FIG. 4 wherein balloon 420 has first diameters 400, which contact vessel wall 100, and second diameters 450 which do not contact with vessel wall 100. The term "a second diameter" is nominal as the "second diameter" represents the diameter, whether identical or different, in the regions between the first diameters that are not in contact with the vessel wall. Other types of balloon catheters may be used in the embodiments of the present invention. In some embodiments, the balloon is microporous.

The embodiments of the present invention are particularly suited to hydrophobic drugs. Particles which are composed of a large fraction of drug are less of an embolic hazard if the drug is water soluble as the particle is likely to dissolve and disappear quickly, and/or quickly dissolve to an extent that the particle size is reduced below a level considered to be an embolic hazard. In some embodiments, the drugs used are those with a solubility in PBS at 37° C. of not more than 1 mg/ml, preferably not more than 0.5 mg/ml, more preferably, not more than 0.1 mg/ml, and even more preferably, not more than 50 µg/ml. In some embodiments, the hydrophobic drugs are selected from the group consisting of zotarolimus, everolimus, sirolimus, biolimus A9, deforolimus, AP23572, tacrolimus, temsirolimus, pimecrolimus, novolimus, myolimus, paclitaxel, protaxel, compounds having the structure of rapamycin but with a substituent at the carbon corresponding to the 42 or 40 carbon, derivatives of any of the preceding drugs, and any combinations thereof. With respect to compounds having the structure of rapamycin but with a substituent at the carbon corresponding to the 42 or 40 carbon, the 42 or 40 carbon does not refer to two different carbon atoms located on the rapamycin molecule, but the same carbon, as illustrated below, with a different label depending upon the numbering scheme used.

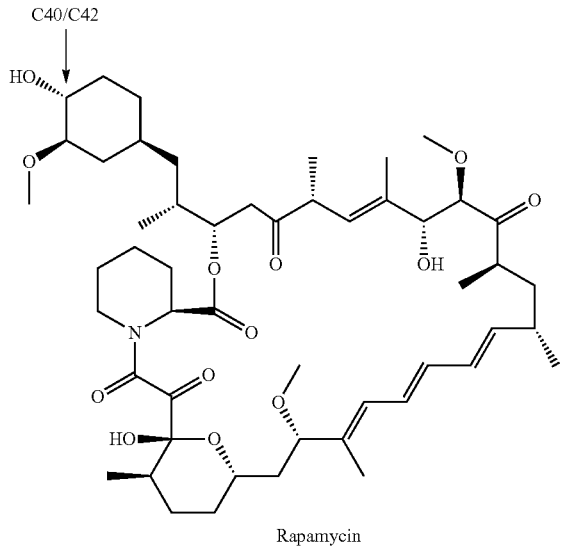 [SMILES: CO[C@H]1C[C@@H]2CC[C@@H](C)[C@@](O)(O2)C(=O)C(=O)N2CCCC[C@H]2C(=O)O[C@H]([C@H](C)C[C@@H]2CC[C@@H](O)[C@H](OC)C2)CC(=O)[C@H](C)/C=C(\C)[C@@H](O)[C@@H](OC)C(=O)[C@H](C)C[C@H](C)/C=C/C=C/C=C/1C]

Rapamycin

The hydrophobic drug is dissolved in a mixture of at least two solvents. The key to obtaining in situ formation of microspheres of drugs is the precipitation of the drug as microspheres onto the substrate. In order to get the drug to precipitate out of the solution, the first solvent is chosen that is a relatively "poor solvent" for the drug compared to the second solvent. In other words, the solubility of the drug in the first solvent is less than in the second solvent. In some embodiments, the drug is at least 10 times less soluble, preferably at least 50 times less soluble, more preferably at least 100 times less soluble, and even more preferably, at least 1000 times less soluble in the first solvent than in the second solvent. In some embodiments, the drug has a solubility of not more than 2000 mg/liter, more preferably not more than 200 mg/liter, and even more preferably, not more than 20 mg/liter in the first solvent.

The first solvent is less volatile than the second solvent. In some embodiments, the second solvent has a vapor pressure, determined at the temperature and pressure conditions under which coating application occurs, but typically at 20 to 25° C. and about one atmosphere, that is at least 20 torr greater than the first solvent, more preferably at least 50 torr greater, and even more preferably at least 100 torr greater. In some embodiments, the first solvent has a vapor pressure of not less than 0.5 torr, more preferably not less than 10 torr, and even more preferably, not less than 20 torr. In some embodiments, the vapor pressure of the first solvent(s) is not more than 25 torr. In some embodiments the second solvent is at least 2 times more volatile, preferably at least 50 times more volatile, more preferably at least 100 or 200 times more volatile, and even more preferably at least 500 or 750 times more volatile than the first solvent. The term "10 times more volatile" will refer to a vapor pressure that is 10 times higher when measured under the same conditions, and in some embodiments, when measured at any temperature from 20° C. to 25° C. and at about one atmosphere.

The second solvent is a good solvent for the drug, and is more volatile than the first solvent which is a poor solvent for the drug. In other words, the solubility of the drug in the second solvent is greater than the solubility in the first solvent. In some embodiments, the drug is at least 10 times more soluble, preferably at least 50 times more soluble, more preferably at least 100 times more soluble, and even more preferably, at least 1000 times more soluble in the second solvent than in the first solvent. In some embodiments, the second solvent is a good solvent if the drug has a solubility of not less than 500 mg/liter, more preferably not less than 5,000 mg/liter, and even more preferably, not less than 50,000 mg/liter.

The second solvent is more volatile than the first solvent. In some embodiments, the vapor pressure of the second solvent is not more than 422 torr, and preferably not more than 200 torr. In some embodiments, the vapor pressure of the second solvent is not more than 50 torr. In some embodiments, the vapor pressure of the second solvent is not less than 125 torr. The one or more second solvent(s) may be selected from the group consisting of methanol, ethanol, isopropanol, 1-propanol, acetone, 2-butanone, diethyl ether, tetrahydrofuran, methyl acetate, and ethyl acetate.

The hydrophobic drug is dissolved in the mixture of the first and second solvents to form a homogeneous or substantially homogeneous coating solution. The coating solution may also include a suspending agent, and/or a binder. The suspending agent may be a surfactant. A homogenous coating solution is one in which a sample taken from any location in the solution would have the same composition as a sample taken from any and all other locations in the solution, but that some variation from exact duplication of composition might be found.

The mass of drug added to the mass of the first solvent will depend upon the solubility of the drug in the first solvent. Obviously, the less soluble the drug, the more of the first solvent may be used. Furthermore, the mass ratio of the drug to the second solvent will also depend upon the drug's solubility in the second solvent. The more soluble the drug in the second solvent, the less of the second solvent may be used. The mass ratio of the drug to the first solvent may range from about 1:99 to about 50:50. The mass ratio of the first solvent to the second solvent will depend upon the solubility of the drug in the first solvent, the miscibility of the first solvent and the second solvent, and the solubility of the drug in the mixture of the first and second solvents. The coating solution is homogeneous, and therefore the ratio of the solvents cannot be such that the drug precipitates from solution before being used to form the coating layer.

The coating solution optionally includes one or more suspending agents and/or one or more binders.

With respect to the suspending agents mentioned in the summary of the invention, polysorbates are a group of oleate esters of sorbitol and its' anhydrides condensed with polymers of ethylene oxide. Polysorbates are used as emulsifiers and surfactants in food, pharmaceuticals and cosmetics. Examples include polysorbate 20, polysorbate 60, and polysorbate 80 the specifications of which are all listed in the USP. Poloxamers are tri-block copolymers with a central block of poly(propylene oxide) (PPO) and with a block of poly(ethylene oxide) (PEO) on each side where the PEO blocks are usually of the same length in terms of number of constitutional units. Poloxamers of types 124, 188, 237, 338, and 407 are specified by a monograph in the National Formulary. Polyoxyl 35 Castor Oil, USP is also known under the BASF trade name CREMOPHOR EL™. It is a non-ionic solubilizer made by reacting 35 moles of ethylene oxide with each mole of caster oil. Other suspending agents are sodium carboxymethyl cellulose, carboxymethyl cellulose derivatives, Vitamin E TPGS, ascorbyl palmitate, fatty alcohols, fatty esters, tocopherols, and phospholipids.

In addition to the binders mentioned in the summary of the invention, other binders which may be used individually or in combination with any other binders disclosed herein include, but are not limited to, poly(vinyl pyrrolidone-co-vinyl acetate), gelatin, maltrodextrin, starch, hydroxypropyl methyl cellulose, other cellulose derivatives, and combinations thereof. Binders as used herein may be molecules, oligomers, and/or polymers. For those binders which are polymers, such as poly(vinyl pyrrolidone) or hydroxyethyl cellulose, the molecular weight of the polymer should be low enough that it dissolves readily (although the application of heat may be required), with a useful viscosity, and still functions as a binder. In some embodiments, the molecular weight of the polymer, expressed as a number average molecular weight, is about 30,000 or less, preferably about 20,000 or less, and even more preferably, about 10,000 or less. In some embodiments, the above number average molecular weight limitations are also applicable to a suspending agent. In some embodiments, the binder and/or suspending agent may have a number average molecular weight in the range of about 5000 to about 8000, and in still other embodiments, the range may be from about 1000 to about 5000.

If binders or suspending agents are used, the mass ratio of suspending agent to drug is not more than 10:1 and typically much smaller, preferably not more than 5:1, more preferably 3:1, and even more preferably not more than 2:1. In some embodiments the mass ratio of suspending agent to drug is not more than 1:1. The lower limit of suspending agent to drug may be about 1:1000, preferably 1:500, and more preferably 1:50. The mass ratio of binder to drug may be at least 1:500, preferably at least 1:100, and more preferably at least 1:20, and not more than 1:4, preferably not more than 1:5, and even more preferably not more than 1:1. Embodiments of the invention encompass all ranges of suspending agent and all ranges of binder that may be obtained by combining the lower and upper limits listed above.

In some embodiments, the coating solution consists of only the hydrophobic drug and the solvents, while in other embodiments the coating solution consists of the solvents, the hydrophobic drug, and optionally the binder and/or the suspending agent. Some suspending agents may also act as binders so in some embodiments both functions are accomplished with one substance. In some embodiments, the binder and the suspending agent are different substances than the hydrophobic drug, and in others, the binder and suspending agent are different substances from each other as well as both being different from the hydrophobic drug. The coating solution may optionally include other excipients, such as, but not limited to, lubricants, anti-static agents, anti-tack agents, anti-foaming agents, stabilizers, anti-oxidants, and/or additives for pH adjustment.

The coating layer formed has the same composition as the solution used in the formation of the coating layer except that the solvents are removed, or essentially removed. In other words, some residual solvent (up to about 7%) may be present in the resulting coating layer. In some embodiments, the coating layer may contain between 0.001% and 2% residual solvent.

In some embodiments, the coating solution, and as a result the coating layer formed there from, may be free of polymers and/or other substances having a number average molecular weight of about 30,000 or more, preferably about 20,000 or more, and even more preferably, about 10,000 or more. In still other some embodiments, the coating solution and the coating or coating layer formed there from, include only polymers and/or substances of a number average molecular weight of less than 8,000, preferably less than 7,000, and more preferably, less than 5,000.

The coating layers may have a drug loading between 10 to 1000 $\mu g/cm^2$, and preferably 50 to 750 $\mu g/cm^2$. In some embodiments, the drug loading may be in the range from 100 to 600 $\mu g/cm^2$, and in other embodiments, in the range of 150 to 600 $\mu g/cm^2$. In still other embodiments, the drug loading in the coating layer may be from 250 to 550 $\mu g/cm^2$, or more narrowly from 300 to 500 $\mu g/cm^2$. Embodiments of the present invention also encompass a coating with a drug loading in any of the above drug loading ranges.

The coating solution may be disposed over the surface of the substrate by procedures such as spraying the solution onto the substrate, immersing or dipping the substrate in the solution, dripping the solution onto the surface, brushing or wiping the surface with the solution, rolling the device in the solution, ink-jet application of the solution, silk screening, or direct fluid dispensing or pipetting of the solution onto the surface. Such coating procedures are well-known in the art. If spraying is used as an application method, the solution may be atomized with a compressed gas (non-limiting examples of compressed gases include, air, nitrogen, or argon). Multiple passes or applications may be required to obtain the desired coating thickness or the desired mass on the substrate.

The solvents are removed, or substantially removed to form the coating layer. The solvents are removed by evaporation. Either simultaneously with and/or after disposing the solution over the substrate, the solvent evaporation may be enhanced any one or any combination of the following: a gas or fluid flow over the surface to remove the solvent where the gas or fluid may be at or above ambient temperature; heating the device such that the device is at a temperature above ambient temperature; placing the device in an environment that is above ambient temperature; and placing the coated substrate under conditions of reduced pressure, such as a vacuum. Ambient temperature is from about 20° C. to about 25° C. Examples of temperature ranges above ambient include, without limitation, 30° C. to 100° C., 35° C. to 65° C., and 40° C. to 60° C. The more volatile of the solvents preferentially evaporates, with the result being the drug exceeds it's solubility limit in the remaining solvent and precipitates out as microspheres.

Figure 6:
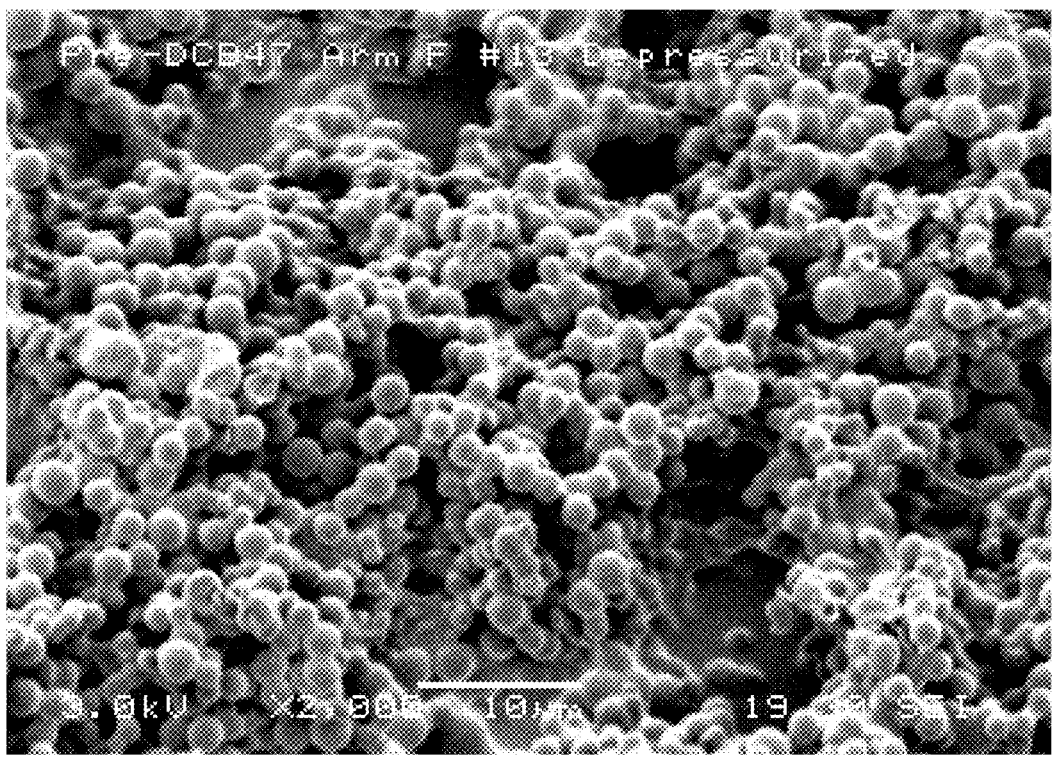
FIG. 6 is an exemplary coating of the present invention on a balloon surface as viewed under SEM.

As used herein with reference to the methods, coatings or devices of the various embodiments of the present invention, the terms "particle," "micro-sphere," "microparticles," "microcapsules," "nanoparticles," "nanocapsules," "nanoshells," and "nanospheres," will refer to pieces of matter, typically spherical or approximately spherical (but not necessarily so limited), which are individually discrete and identifiable in the coating layers or coated devices of the present invention. An example is provided by the SEM micrograph of FIG. 6. As shown in FIG. 6, although the particles may form agglomerates or appear to form a necklace or string of particles, the individual particles are still distinguishable from their surroundings.

In some embodiments, the coating consists of primarily particles, or the majority of the coating is particles. In other embodiments, the particles may be embedded in a film or matrix, but are released as individual particles or aggregates of a limited number of particles because the binder film quickly dissolves.

The particles may have any one of various configurations. Examples include, without limitation, the drug and any excipients such as binder and/or suspending agent being uniformly or substantially uniformly distributed throughout the particle. Such type of particles are often referred to as "matrix type" or monolithic type particles. The drug may be non-uniformly distributed throughout the particle. In other embodiments the drug may form a core with most of the excipients such as the binder and/or the suspending agent forming a shell around the core, or vice versa. The particles may also be any combination of the above, that is drug uniformly or non-uniformly distributed in a core with a shell of excipients surrounding the core. In some embodiments, the suspending agent, which may be a surfactant, may form a sort of "micelle" on the surface with the hydrophobic drug being encapsulated within the core and the suspending agent forming a shell around the drug. Other types of core/shell constructs such as, without limitation, micelles, worm micelles, liposomes and polymerosomes, may be formed depending upon the selection of binders and/or suspending agents.

If the prefix "micro" is used, for example a "microparticle," this generally refers to a particle with a maximum cross-sectional dimension of from 1 μm to about 1000 μm, or alternatively, a plurality of particles for which the volume average diameter is in the range of 1 μm to 1000 μm. The use of the prefix "nano" is defined likewise such that a nanoparticle (or nanoshell, nanocapsule, or the like) is a particle with a maximum cross-sectional dimension of from 1 nm to 1000 nm, or alternatively, a plurality of particles for which the volume average diameter is in the range of 1 nm to 1000 nm. In some embodiments, when the term "micro" or "nano" is used with reference to a plurality of particles (capsules, shells, etc.), the distribution is such that not more than 30% of the particles (capsules, shells, etc.) are above the upper limit, that is 1000 μm or 1000 nm, respectively, based upon the volume average distribution.

The particles in the coating that are formed in situ during the coating formation may be of essentially uniform size (that is D90/D10 based upon the volume distribution is not more than 10, preferably not more than 8, and even more preferably, not more than 5), or may vary in particle size distribution. The particles may include essentially the same components as the coating solution except the solvent (although some residual solvent may remain). The mass ratio of the drug to the excipients, that is the optional binder and/or suspending agent and other excipients, may parallel the ratio in the coating solution used to form the coating, or the binder or suspending agent may be preferentially excluded from the particles. In some embodiments, the particles may be enriched in drug such that the drug mass fraction is about 5% or greater, about 10% or greater, or about 20% or greater than the drug fraction in the coating solution exclusive of solvents. In some embodiments, the ratio of the drug to the other excipients may be essentially the same for all of the particles. In other embodiments, some of the binder may serve to bind the particles to each other and/or to the surface of the substrate or to a previously applied coating layer.

Embodiments of the present invention also encompass medical devices, including expandable medical devices, with a coating including a hydrophobic drug in the form of particles as described herein (also referred to as "a particulate hydrophobic drug"). In some embodiments, upon expansion of the device, 30% or fewer of the drug particles that are cast off from the coating have a diameter of greater than 30 μm based upon the volume average distribution, preferably not more than 20 μm, more preferably not more than 15 μm, even more preferably not more than 10 μm, and most preferably not more than 8 μm. The phrases "drug particles cast off" and "particles that are cast off" refer to those particles that are shed, released, or that otherwise disassociate from the surface of the coated device upon expansion as determined by the test method described in Example 2. As Example 2 describes below, the volume distribution of the particles was determined from a number average distribution, and such approximation shall be considered to be sufficient to represent the volume distribution. In some embodiments, 20% or fewer of the drug particles cast off from the coating have a diameter of greater than 30 μm based upon the volume average distribution, preferably not more than 20 μm, more preferably not more than 15 μm, even more preferably not more than 10 μm, and most preferably not more than 8 μm. The particles counted in the method of Example 2 may actually be agglomerates of two or more individual particles such as those observed on the surface as described in Example 5. Thus, it is believed that under in vivo conditions of shear flow of blood or other fluid, the agglomerates may readily separate into the primary particles which together form the agglomerate. The method of Example 2 counts particles that are not completely dissolved during the test method, and thus particles which quickly dissolved would not be counted.

The coating solution may be deposited directly onto the surface of the substrate, or the coating solution may be deposited onto a pre-existing coating on the surface of the device, such as a primer layer. For a stent, an example of the substrate surface would be the surface of the "device body," that is the functional device without a coating or layer of material different from that of which the device body is manufactured has been applied. For a balloon, the substrate surface would be the surface of the balloon measured when inflated to its nominal pressure. A "primer layer" refers to a coating consisting of a material, typically a polymer, that exhibits good adhesion characteristics with regard to the material of which the substrate is manufactured and good adhesion characteristic with regard to whatever material is to be coated on the substrate.

The coating solution may be disposed over all of the outer surface of the device, or a portion of the outer surface of the device. The coating may be continuous or discontinuous (uncoated patches or "holes" may exist), and the coating may be of substantially uniform thickness. A typical coating thickness may be in the range of about 0.1 to about 20 microns. For an implantable medical device or a medical device which is inserted into the body for a transitory time period such as a balloon catheter, "outer surface" is meant any surface however spatially oriented that is in contact with bodily tissue or fluids. In some embodiments, the coating may be deposited on selective portions of the outer surface. As a non-limiting example, for a stent the coating may be selectively formed on the abluminal surface, that is the surface in contact with the vessel walls. Another non-limiting example is selectively coating the cylindrical surface corresponding to the working length of a balloon of a balloon catheter, that is the surface area of the balloon that would contact the lumen wall. As used herein, unless expressly stated otherwise, the phrases "coating a catheter balloon," or a "coated catheter balloon," will refer to the process of coating, or a coating formed on, the entire surface, or a portion of the surface, of the balloon of the balloon catheter, but not including the catheter. With respect to other medical devices, unless specified otherwise, the coating covers all of or substantially all of the outer surface of the substrate. For any of the above embodiments, the coating comprising the in situ formed drug particles may have another coating layer that has been disposed over this layer. However, in preferred embodiments, the coating with the drug particles is the outermost coating that would be in contact with tissue and/or potentially other bodily fluids.

In any of the above embodiments, the coated device may release 60% of the drug loading (total content of drug, or the amount of drug per device) within the first hour after expansion, preferably 70% of the total drug loading, and even more preferably 80% of the total drug loading. In other embodiments, any of the coated devices as described above may release not less than 80% of the drug within the first 30 minutes following the initiation of expansion. In still other embodiments, any of the coated devices as described above may release not less than 80% of the drug within the first 5 minutes following the initiation of expansion. Drug release or delivery is defined as transfer of the drug from the delivery interface, that is the coating to the tissue and/or lumen. In other words, the drug remaining on the device if removed from the patient (or subject) is the unreleased drug, all of the remainder having been released. As noted above, the drug may be released as particles.

As noted above, the use of an appropriate coating solution results in the in situ formation of microspheres of the appropriate size such that the microspheres are cast off as individual microspheres or aggregates. Without being bound by any particular theory, it is believed that the in situ formation of microspheres results from the relative volatilities of the first and second solvents, the relative solubilities of the drug in the first and second solvents, the absolute volatility of the second solvent, and the rate of evaporation of the second solvent. The optimization of a traditional coating formulation would not necessarily produce a coating in which microspheres were formed in situ. It is believed that the formation of microspheres requires a difference in the volatility of the two solvents as well as a difference in the solubility of the two solvents. It is believed that the microsphere formation of the correct size is controlled by the evaporation of the more volatile solvent at the correct rate. If the evaporation is too fast, it is believed that the microspheres of the hydrophobic drug would not be formed, while if the evaporation is too slow, the microspheres formed may be too large in size. Moreover, the two solvents mixed together must produce a homogenous or substantially homogeneous coating solution. In addition, it is believed that the choice of suspending agent may aid in the dispersion of the microspheres as individual particles or small aggregates of individual particles. Example 2 and FIG. 6 which are described below illustrate that more particles were obtained in the smaller particle sizes using a method which is an embodiment of the present invention as compared to traditional coating methods.

Embodiments of the present invention also include methods of treatment with any of the coated devices described herein. If a DCB, the balloon is typically attached to the end of a catheter. The catheter is introduced into a patient's vasculature at some point, which, depending upon the area to be treated, may be remote from the target site, e.g., into the femoral artery of the leg where the target is in the vicinity of the heart. The catheter is guided to the treatment site where the balloon is then inflated, typically using a liquid medium, such as water or normal saline solution. However, inflation of the balloon may be effected by any means known or as shall become known in the art. Upon expansion of the balloon, the coating comes into contact with the lumen walls and the drug is delivered. The inflation of the balloon may also expand the lumen. A coated stent may be similarly delivered after being crimped onto a balloon if balloon-expandable, or covered with a sheath or some other restraint, if self-expandable. Embodiments of the present invention encompass the use of a drug coated balloon catheter, for example and without limitation, in the neurological, carotid, coronary, iliac, femoral, popliteal, or other peripheral vasculature. Stents coated as described herein may be used for treatment in coronary or peripheral vasculature. Stents and/or balloons, as well as other medical devices, coated as described herein may be used for treatment of peripheral artery disease (PAD), in peripheral arteries such as the superficial femoral artery (SFA).

With regard to the various embodiments of the present invention, zotarolimus and everolimus, both immunosuppressive macrolide antibiotics, are preferred drugs, diethanolamine-carboxymethyl cellulose (DEA-CMC, ratio DEA/CMC approximately 25/75 (w/w)) is a preferred suspending agent, deionized water is a preferred first solvent, and methanol is a preferred second solvent. A preferred substrate or device is a catheter balloon. A preferred method of treatment is the treatment of conditions in the peripheral vasculature and specifically the SFA.

Examples of drugs that may be suitable for use in the methods and devices of this invention depending, of course, on the specific disease being treated, and with consideration of the physical properties of the drug, include, without limitation, anti-restenosis, pro- or anti-proliferative, anti-inflammatory, anti-neoplastic, antimitotic, anti-platelet, anticoagulant, antifibrin, antithrombin, cytostatic, antibiotic, anti-enzymatic, anti-metabolic, angiogenic, cytoprotective, angiotensin converting enzyme (ACE) inhibiting, angiotensin II receptor antagonizing and/or cardioprotective drugs.

Examples of antiproliferative drugs include, without limitation, actinomycins, taxol, docetaxel, paclitaxel, sirolimus (rapamycin), biolimus A9 (Biosensors International, Singapore), deforolimus, AP23572 (Ariad Pharmaceuticals), tacrolimus, temsirolimus, pimecrolimus, zotarolimus (ABT-578), 40-O-(2-hydroxy)ethyl-rapamycin (everolimus), 40-O-

(3-hydroxypropyl)rapamycin (a structural derivative of rapamycin), 40-O-[2-(2-hydroxy)ethoxy]ethyl-rapamycin (a structural derivative of rapamycin), 40-O-tetrazole-rapamycin (a structural derivative of rapamycin), 40-O-tetrazolylrapamycin, 40-epi-(N-1-tetrazole)-rapamycin, and pirfenidone.

Examples of anti-inflammatory drugs include both steroidal and non-steroidal (NSAID) anti-inflammatories such as, without limitation, clobetasol, alclofenac, alclometasone dipropionate, algestone acetonide, alpha amylase, amcinafal, amcinafide, amfenac sodium, amiprilose hydrochloride, anakinra, anirolac, anitrazafen, apazone, balsalazide disodium, bendazac, benoxaprofen, benzydamine hydrochloride, bromelains, broperamole, budesonide, carprofen, cicloprofen, cintazone, cliprofen, clobetasol propionate, clobetasone butyrate, clopirac, cloticasone propionate, cormethasone acetate, cortodoxone, deflazacort, desonide, desoximetasone, dexamethasone, dexamethasone dipropionate, dexamethasone acetate, dexmethasone phosphate, momentasone, cortisone, cortisone acetate, hydrocortisone, prednisone, prednisone acetate, betamethasone, betamethasone acetate, diclofenac potassium, diclofenac sodium, diflorasone diacetate, diflumidone sodium, diflunisal, difluprednate, diftalone, dimethyl sulfoxide, drocinonide, endrysone, enlimomab, enolicam sodium, epirizole, etodolac, etofenamate, felbinac, fenamole, fenbufen, fenclofenac, fenclorac, fendosal, fenpipalone, fentiazac, flazalone, fluazacort, flufenamic acid, flumizole, flunisolide acetate, flunixin, flunixin meglumine, fluocortin butyl, fluorometholone acetate, fluquazone, flurbiprofen, fluretofen, fluticasone propionate, furaprofen, furobufen, halcinonide, halobetasol propionate, halopredone acetate, ibufenac, ibuprofen, ibuprofen aluminum, ibuprofen piconol, ilonidap, indomethacin, indomethacin sodium, indoprofen, indoxole, intrazole, isoflupredone acetate, isoxepac, isoxicam, ketoprofen, lofemizole hydrochloride, lomoxicam, loteprednol etabonate, meclofenamate sodium, meclofenamic acid, meclorisone dibutyrate, mefenamic acid, mesalamine, meseclazone, methylprednisolone suleptanate, momiflumate, nabumetone, naproxen, naproxen sodium, naproxol, nimazone, olsalazine sodium, orgotein, orpanoxin, oxaprozin, oxyphenbutazone, paranyline hydrochloride, pentosan polysulfate sodium, phenbutazone sodium glycerate, pirfenidone, piroxicam, piroxicam cinnamate, piroxicam olamine, pirprofen, prednazate, prifelone, prodolic acid, proquazone, proxazole, proxazole citrate, rimexolone, romazarit, salcolex, salnacedin, salsalate, sanguinarium chloride, seclazone, sermetacin, sudoxicam, sulindac, suprofen, talmetacin, talniflumate, talosalate, tebufelone, tenidap, tenidap sodium, tenoxicam, tesicam, tesimide, tetrydamine, tiopinac, tixocortol pivalate, tolmetin, tolmetin sodium, triclonide, triflumidate, zidometacin, zomepirac sodium, aspirin (acetylsalicylic acid), salicylic acid, corticosteroids, glucocorticoids, tacrolimus and pimecrolimus.

Examples of antineoplastics and antimitotics include, without limitation, paclitaxel, docetaxel, methotrexate, azathioprine, vincristine, vinblastine, fluorouracil, doxorubicin hydrochloride and mitomycin.

Examples of anti-platelet, anticoagulant, antifibrin, and antithrombin drugs include, without limitation, heparin, sodium heparin, low molecular weight heparins, heparinoids, hirudin, argatroban, forskolin, vapiprost, prostacyclin, prostacyclin dextran, D-phe-pro-arg-chloromethylketone, dipyridamole, glycoprotein IIb/IIIa platelet membrane receptor antagonist antibody, recombinant hirudin and thrombin, thrombin inhibitors such as ANGIOMAX® (bivalirudin, from Biogen), calcium channel blockers such as nifedipine, colchicine, fish oil (omega 3-fatty acid), histamine antagonists, lovastatin, monoclonal antibodies such as those specific for Platelet-Derived Growth Factor (PDGF) receptors, nitroprusside, phosphodiesterase inhibitors, prostaglandin inhibitors, suramin, serotonin blockers, steroids, thioprotease inhibitors, triazolopyrimidine, nitric oxide or nitric oxide donors, super oxide dismutases, super oxide dismutase mimetic and 4-amino-2,2,6,6-tetramethylpiperidine-1-oxyl (4-amino-TEMPO).

Examples of cytostatic or antiproliferative drugs include, without limitation, angiopeptin, angiotensin converting enzyme inhibitors such as captopril, cilazapril or lisinopril, calcium channel blockers such as nifedipine; colchicine, fibroblast growth factor (FGF) antagonists; fish oil (ω-3-fatty acid); histamine antagonists; lovastatin, monoclonal antibodies such as, without limitation, those specific for Platelet-Derived Growth Factor (PDGF) receptors; nitroprusside, phosphodiesterase inhibitors, prostaglandin inhibitors, suramin, serotonin blockers, steroids, thioprotease inhibitors, triazolopyrimidine (a PDGF antagonist) and nitric oxide.

Examples of ACE inhibitors include, without limitation, quinapril, perindopril, ramipril, captopril, benazepril, trandolapril, fosinopril, lisinopril, moexipril and enalapril.

Examples of angiotensin II receptor antagonists include, without limitation, irbesartan and losartan.

Other therapeutic drugs that may find beneficial use herein include, again without limitation, alpha-interferon, genetically engineered endothelial cells, dexamethasone, antisense molecules which bind to complementary DNA to inhibit transcription, and ribozymes, antibodies, receptor ligands such as the nuclear receptor ligands estradiol and the retinoids, thiazolidinediones (glitazones), enzymes, adhesion peptides, blood clotting factors, inhibitors or clot dissolving drugs such as streptokinase and tissue plasminogen activator, antigens for immunization, hormones and growth factors, oligonucleotides such as antisense oligonucleotides and ribozymes and retroviral vectors for use in gene therapy, antiviral drugs and diuretics.

EXAMPLES

The following examples are given to aid in understanding the invention, but it is to be understood that the invention is not limited to the particular materials or procedures of the examples.

Example 1

Currently marketed drug coated balloons for use in the coronary artery were evaluated. Each of the drug coated balloons was "delivered" to a deployment site in a plastic model of the coronary artery vasculature filled with PBS at 37° C., but not deployed. The number of particles in the solution was determined using a HIAC ROYCO™ particle counter. In another phase of the experiment, the DCBs were delivered and "deployed" within a model of the coronary artery filled with PBS at 37° C., that is the balloons were inflated to a nominal pressure, held for 30 seconds duration, and then deflated and removed from the model. The particle count of the solution was measured after inflation.

FIGS. 1 and 2 are histograms of the results for the particle counts with and without balloon inflation for particles in the 10-25 micron and in the 25-50 micron range, respectively. As illustrated in FIGS. 1 and 2, the number of particles in the solution is significant. The drug coated balloons that were tested were 3×18 mm VISION Rx coronary dilatation catheters from Abbott Vascular coated with 2/1/0.4 zotarolimus/PVP/glycerol at a drug dose density of 300 ug/cm², the product called ELUTAX™ made by Aachen Resonance, the IMPACT FALCON™ made by Invatec, and SEQUENT PLEASE™ made by B. Braun. The number of balloons for each product was not identical for all of the tests (the "n" number of samples varied).

Example 2

A coating solution was formed by mixing the following: 0.30 grams of diethanolamine-carboxymethyl cellulose (DEA-CMC) with a ratio of DEA/CMC 25/75 (w/w); 4.32 grams of deionized water; 7.38 grams of methanol; and 3.00 grams of a 10 weight % solution of zotarolimus in methanol. First, the DEA-CMC was added to the deionized water and agitated until it dissolved. Then the solution was diluted with the methanol. Finally, the solution of methanol and zotarolimus was added. The resulting solution included zotarolimus and DEA-CMC at a 50:50 mass ratio in a solvent of 70% by weight methanol and 30% by weight water. The solution was clear and homogeneous.

Balloon catheters, 6×40 mm 0.035" AGILTRAC® (Abbott Vascular, Temecula, Calif.), non-silicone coated, were washed by sonicating in isopropanol and then subjected to an argon plasma treatment. To obtain a 300 µg/cm² zotarolimus loading on a catheter balloon, the coating solution was dispensed by direct fluid dispensing of approximately 133.4 µl of solution onto the catheter balloon. The direct fluid dispenser dispensed the solution at a rate of 63.2 µl/min from the dispenser tube. The dispenser tube was surrounded by an annulus through which nitrogen flowed at a rate of 325 ml/min to enhance the evaporation of solvent. Thus the dispensing of the fluid occurred concurrently with the application of a flow of nitrogen over the coating. The entire balloon surface was not coated but only the surface area represented by the working length. After the coating solution was disposed over the surface, the balloons were placed in an oven at 50° C. for one hour. The balloon was then pleated and folded, a sheath was placed over the balloon, and the catheter and balloon assembly was packaged under argon. The packaged balloon and catheter assembly was then sterilized by electron beam irradiation using a 25 KGy dose of radiation.

The coated balloon was evaluated for "particles" that were cast off or shed from the balloon. The drug coated balloons were lowered into a beaker containing 140 ml of PBS at 37° C., inflated to a nominal pressure, held for 30 seconds duration, and then the balloon was raised out of the solution. The particle count of the solution was measured after inflation. A Hiac Royco particle counter was utilized which provided the number of particles in various size ranges. The number counts in each of the particle size ranges were converted to an approximate volume average particle size distribution by taking the particle counts in each range, assigning the mid-range diameter to all of the particles in the group, and converting this to a volume assuming a spherical geometry.

Figure 5:
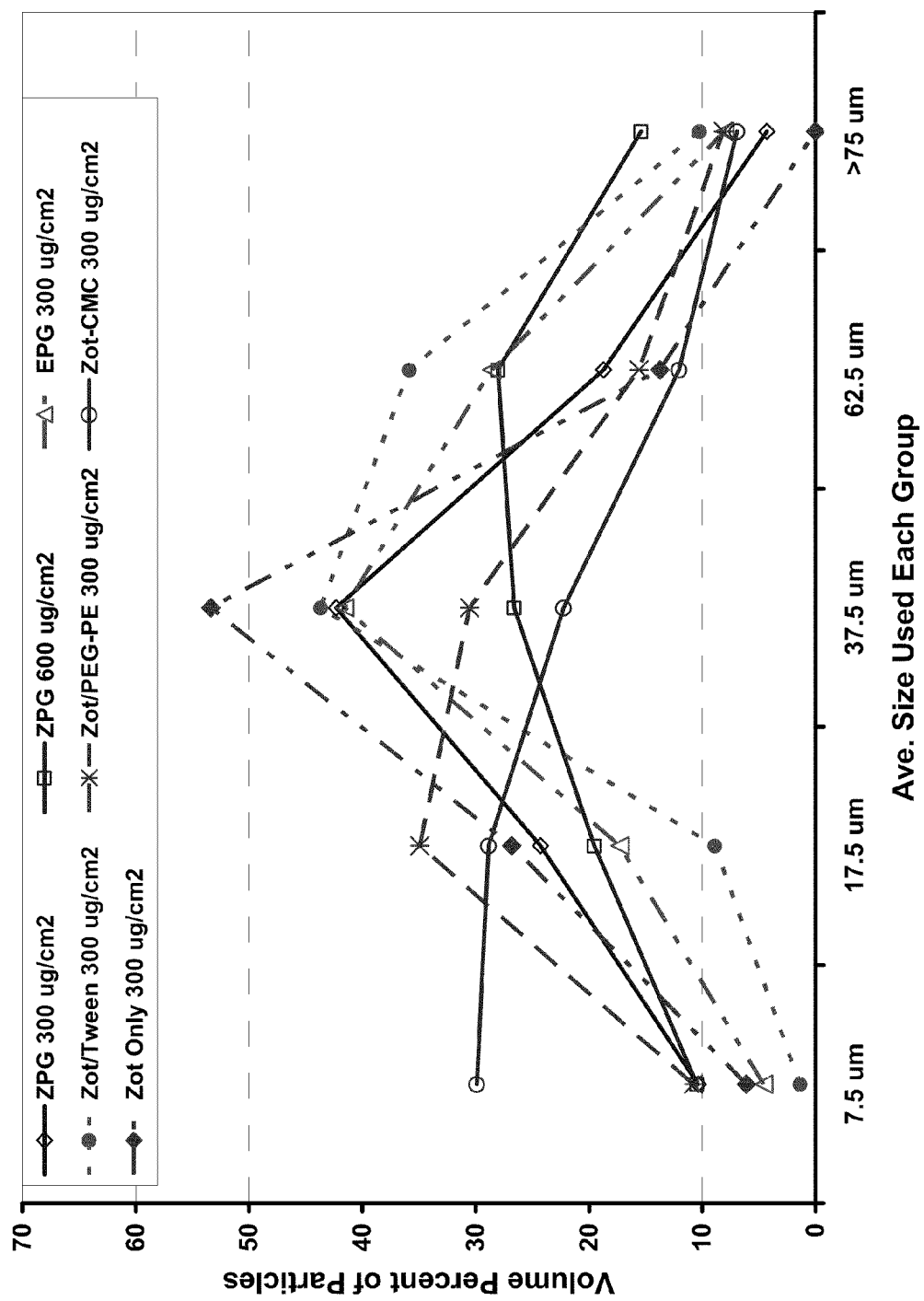
FIG. 5 is a graph of the volume average particle size distribution for particles cast off of an exemplary drug coated peripheral balloon of the present invention.

The results of the volume size distribution are shown in FIG. 5 along with comparative data from other coated balloon formulations. Table 1 below provides the formulations corresponding to the different data series presented in FIG. 5.

TABLE 1

Formulations for FIG. 5

| Series | Formulation | Solvent | Microsphere Coating or Traditional Coating |
|---|---|---|---|
| ZPG | Zotarolimus formulated with polyvinylpyrrolidone and glycerol (2/1/0.4 weight ratio) | Acetone/ Ethanol | Traditional |
| EPG | Everolimus formulated with polyvinylpyrrolidone and glycerol (2/1/0.4 weight ratio) | Acetone/ Ethanol | Traditional |
| Zot/Tween | Zotarolimus and Tween-20 (3/1 w/w) | Acetone/ Ethanol | Traditional |
| Zot/ PEG-PE | Zotarolimus and 1,2-distearoyl-sn-glycero-3-phosphoethanolamine-N-[methoxy(polyethylene glycol)-2000](ammonium salt) (1/1 w/w) | Acetone/ Methanol | Traditional |
| Zot/CMC | Zotarolimus and diethanolamine-carboxymethylcellulose (1:1 or 1:2 weight ratio) | Deionized Water/ Methanol | Microsphere |
| Zot only | Zotarolimus | Acetone/ Ethanol | Traditional |

In FIG. 5, the line labeled "Zot-CMC" is the only microsphere formulation, the other formulations being traditional coating formulations in which the components are dissolved in a solvent and disposed over the balloon surface. The traditional coatings were made using a solution of two good solvents, that is acetone and ethanol. The traditional coating solutions did not include a "poor solvent" of significantly lower volatility than the other. As shown in FIG. 5, the zotarolimus-DEA-CMC formulation exhibited the largest percent of the particles cast off in the 7.5 µm range, based on the volume distribution of particles.

Example 3

A coating solution identical to that made in Example 2 was made. Instead of being deposited on the surface of a catheter balloon, the solution was deposited on a clean glass slide which was placed in an oven at 50° C. for one hour. An optical micrograph at a magnification of 500× was taken. The optical micrograph showed fairly uniform microspheres. Many single microspheres were clearly visible in the micrograph. Subsequently, PBS solution was added to the glass slide, and the release and dispersion of the coating was observed. Dispersion of the microspheres both individually and as aggregates was observed.

It is believed that the use of a suspending agent other than DEA-CMC and/or the inclusion of a surfactant such as PLURONIC® brand tri-block (poly(ethylene oxide-b-poly(propylene oxide)-b-poly(ethylene oxide)) surfactants would improve the dispersion of the particles. It is also believed that many of the larger particles are aggregates or agglomerates of smaller primary particles. It is also believed that many of these aggregates would be readily broken down into the smaller primary particles upon the application of some shear force such as that resulting from the flow of blood through a blood vessel.

Example 4

An example for purposes of comparison was conducted. The experiment followed the procedure of Example 3 with a solution of zotarolimus/polyvinyl pyrrolidone/glycerol (zot/PVP/glycerol) at a weight ratio of 2/1/0.4 being applied to a glass slide. PBS was added to the zot/PVP/glycerol coating on the glass slide and observations were made. Fragments of the coating of various sizes were visually observed rather than particles or aggregates of particles. It was observed that the size distribution of the fragments was a function of the thickness of the coating and the degree of agitation of the solution. The particle size distribution of a coating of this formulation on a catheter balloon is illustrated in FIG. 5 as the dotted-line with the filled diamonds labeled "ZPG 300 ug/cm$^2$."

Example 5

A coating formulation analogous to that of Example 2 was made except that the weight ratio of zotarolimus to DEA-CMC was 1:2 as opposed to the 1:1 ratio used in Example 2. The coating formulation was applied to a 6×40 mm AGIL-TRAC® catheter balloon and placed in an oven at 50° C. for one hour. A scanning electron microscope (SEM) was used to observe the surface of the balloon. Microspheres which appeared to be fairly uniform in size were clearly visible on the surface of the balloon as well as aggregates of microspheres. Individual discrete microspheres could be clearly distinguished. Inspection of the SEM micrograph indicated that the microspheres were on the order of 2-3 microns in diameter based on the two dimensional representation. FIG. 6 is the SEM of the balloon surface. As illustrated in FIG. 6 individual particles approximately spherical in shape can be distinguished from the surroundings.

While particular embodiments of the present invention have been shown and described, it will be obvious to those skilled in the art that changes and modifications can be made without departing from this invention in its broader aspects. Therefore, the claims are to encompass within their scope all such changes and modifications as fall within the true sprit and scope of this invention. Moreover, although individual aspects or features may have been presented with respect to one embodiment, a recitation of an aspect for one embodiment, or the recitation of an aspect in general, is intended to disclose its use in all embodiments in which that aspect or feature can be incorporated without undue experimentation. Also, embodiments of the present invention specifically encompass embodiments resulting from treating any dependent claim which follows as alternatively written in a multiple dependent form from all prior claims which possess all antecedents referenced in such dependent claim (e.g. each claim depending directly from claim 1 should be alternatively taken as depending from any previous claims).

What is claimed is:

1. A method for coating a balloon catheter, the method comprising:
forming a homogeneous coating solution by dissolving a hydrophobic drug having a solubility in phosphate buffered saline of about 1 mg/ml or less than 1 mg/ml in a coating solvent comprising one or more first solvents in which the drug has a solubility of not more than 2000 mg/liter and one or more second solvents in which the drug has a solubility of not less than 10,000 mg/liter, wherein the one or more second solvents is/are more volatile than the one or more first solvents by at least a factor of 2;
disposing the coating solution over a surface of the balloon of the balloon catheter;
removing the one or more second solvents at a temperature and pressure selected such that the drug precipitates from the remaining coating solution as particles of a volume weighted average diameter of 30 microns or less; and
removing the remaining coating solvent;
wherein the coating solution further comprises a suspending agent/surfactant, a binder, or both;
wherein the drug is selected from the group consisting of zotarolimus, everolimus, sirolimus, biolimus A9, deforolimus, ridaforolimus, tacrolimus, temsirolimus, pimecrolimus, novolimus, myolimus, paclitaxel, protaxel, and combinations thereof;
wherein the one or more first solvent(s) is/are selected from the group consisting of water, ethylene glycol, propylene glycol, glycerol, n-butyl alcohol, 2-butyl alcohol, furfuryl alcohol, formamide, methylformamide, and dimethylformamide;
and
wherein the one or more second solvent(s) is/are selected from the group consisting of methanol, ethanol, isopropanol, 1-propanol, acetone, 2-butanone, diethyl ether, tetrahydrofuran, methyl acetate, and ethyl acetate.

2. The method of claim 1, wherein the wt/wt ratio of drug to the one or more first solvents is greater than 1/99 and less than 50/50.

3. The method of claim 1, wherein the coating solution comprises a suspending agent/surfactant.

4. The method of claim 1, wherein the coating solution comprises a binder.

5. The method of claim 1, wherein the one or more second solvents is/are more volatile than the one or more first solvents by at least a factor of 50.

6. The method of claim 1, wherein the one or more second solvents is/are more volatile than the one or more first solvents by at least a factor of 750.

7. The method of claim 3, wherein the suspending agent/surfactant is selected from the group consisting of carboxymethyl cellulose, sodium carboxymethyl cellulose, diethanolamine carboxymethyl cellulose, polysorbates, poly(vinyl alcohol), gelatin, sucrose, phospholipids, pegylated phospholipids, poly(ethylene oxide)-poly(propylene oxide) block copolymers, ascorbyl palmitate, USP grade polyoxyl 35 Castor Oil, tocopherols, and combinations thereof.

8. The method of claim 4, wherein the binder is selected from the group consisting of poly(ethylene glycol), poly(2-hydroxyethyl methacrylate), poly(hydroxypropyl methacrylamide), poly(vinyl alcohol), chitosan, sodium alginate, hydroethyl cellulose, hydroxypropyl cellulose, methyl cellulose, ethyl cellulose, dextran, poly(vinyl pyrrolidone), and combinations thereof.

9. The method of claim 1, wherein the one or more first solvent(s) is/are selected from the group consisting of water, ethylene glycol, propylene glycol, glycerol, formamide, methylformamide, and dimethylformamide.

10. The method of claim 1, wherein the one or more second solvent(s) is/are selected from the group consisting of methanol, ethanol, isopropanol, 1-propanol, acetone, diethyl ether, and tetrahydrofuran.

11. The method of claim 1, wherein disposing the coating solution over the surface of the balloon is accomplished by spraying, rolling, pipetting, brushing, ink jet application, silk screening, direct fluid application, or dip coating.

12. The method of claim 1, further comprising applying a gas stream of air, nitrogen, argon or other inert gas to the balloon.

13. The method of claim 12, wherein the application of the gas stream occurs simultaneously with disposing the coating solution over the surface of the balloon.

14. The method of claim 12, wherein the application of the gas stream occurs after disposing the coating solution over the surface of the balloon.

15. The method of claim 1, wherein the coating solution comprises diethanolamine carboxymethyl cellulose, and the hydrophobic drug is zotarolimus or everolimus.

16. The method of claim 1, wherein the hydrophobic drug is selected from the group consisting of zotarolimus, everolimus, and combinations thereof.

17. The method of claim 3, wherein the suspending agent/surfactant comprises at least one member of the group consisting of lecithin, vitamin E TPGS, PEG-PE, polysorbate 20, polysorbate 60, polysorbate 80, poloxamer 407, and poloxamer 188.

18. The method of claim 3, where the suspending agent/surfactant comprises at least one member of the group consisting of fatty alcohols and fatty esters.

19. The method of claim 16, wherein the first solvent is water, and the second solvent is methanol.

20. The method of claim 11, wherein disposing the coating solution over the surface of the balloon is accomplished by direct fluid application with concurrent application of a gas stream of air, nitrogen, argon, or other inert gas to the surface of the balloon by using an annulus through which the gas stream flows, the annulus surrounding a dispensing tube used in the direct fluid application.

21. A method for coating a balloon catheter, the method comprising:
   forming a homogeneous coating solution by dissolving a hydrophobic drug, the drug being zotarolimus, everolimus, sirolimus, paclitaxel, or a combination thereof, in a coating solvent, the coating solution comprising:
      the coating solvent comprising:
         one or more first solvent(s), each first solvent selected from the group consisting of water, ethylene glycol, propylene glycol, glycerol, n-butyl alcohol, 2-butyl alcohol, furfuryl alcohol, formamide, methylformamide, and dimethylformamide;
         and
         one or more second solvent(s), each second solvent selected from the group consisting of methanol, ethanol, isopropanol, 1-propanol, acetone, 2-butanone, diethyl ether, tetrahydrofuran, methyl acetate, and ethyl acetate;
      and
      a suspending agent/surfactant, a binder, or both;
         wherein the one or more second solvents is/are more volatile than the one or more first solvents by at least a factor of 2;
   disposing the coating solution over a surface of the balloon of the balloon catheter;
   removing the one or more second solvents from the coating solution at a temperature and pressure selected such that the drug precipitates from the remaining coating solution as particles of a volume weighted average diameter of 30 microns or less; and
   removing the remaining coating solvent.

22. The method of claim 21, wherein the coating solution comprises a suspending agent/surfactant selected from the group consisting of carboxymethyl cellulose, sodium carboxymethyl cellulose, diethanolamine carboxymethyl cellulose, polysorbates, poly(vinyl alcohol), gelatin, sucrose, phospholipids, pegylated phospholipids, poly(ethylene oxide) - poly(propylene oxide) block copolymers, ascorbyl palmitate, USP grade polyoxyl 35 Castor Oil, tocopherols, and combinations thereof.

23. The method of claim 21, wherein the coating solution comprises a binder selected from the group consisting of poly(ethylene glycol), poly(2-hydroxyethyl methacrylate), poly(hydroxypropyl methacrylamide), poly(vinyl alcohol), chitosan, sodium alginate, hydroethyl cellulose, hydroxypropyl cellulose, methyl cellulose, ethyl cellulose, dextran, poly (vinyl pyrrolidone), and combinations thereof.

24. The method of claim 22, wherein the coating solution comprises a binder selected from the group consisting of poly(ethylene glycol), poly(2-hydroxyethyl methacrylate), poly(hydroxypropyl methacrylamide), poly(vinyl alcohol), chitosan, sodium alginate, hydroethyl cellulose, hydroxypropyl cellulose, methyl cellulose, ethyl cellulose, dextran, poly (vinyl pyrrolidone), and combinations thereof.

25. The method of claim 21, wherein disposing the coating solution over the surface of the balloon is accomplished by direct fluid application with concurrent application of a gas stream of air, nitrogen, argon, or other inert gas to the surface of the balloon by using an annulus through which the gas stream flows, the annulus surrounding a dispensing tube used in the direct fluid application.

26. The method of claim 1, wherein the particles comprising precipitated drug are individually discrete and identifiable.

27. The method of claim 1, wherein the particles comprising precipitated drug are spherical, or approximately spherical.

28. The method of claim 26, wherein the particles comprising precipitated drug are spherical, or approximately spherical.

29. The method of claim 1, wherein the particles comprising drug are spherical.

30. The method of claim 26, wherein the particles comprising drug are spherical.

31. The method of claim 1, wherein after removal of the solvents, the catheter balloon is pleated, folded, and a sheath placed over the balloon, then optionally sterilized, and subsequently the catheter balloon is placed in a container of water, inflated to nominal pressure, and held for about 30 seconds at nominal pressure before removal; wherein for the particles comprising drug that are cast off the balloon during and after inflation, 30% or fewer have a diameter greater than 30 microns, based upon a volume average distribution.

32. The method of claim 21, wherein the particles comprising precipitated drug are individually discrete and identifiable.

33. The method of claim 21, wherein the particles comprising precipitated drug are spherical, or approximately spherical.

34. The method of claim 32, wherein the particles comprising precipitated drug are spherical, or approximately spherical.

35. The method of claim 21, wherein the particles comprising drug are spherical.

36. The method of claim 32, wherein the particles comprising drug are spherical.

37. The method of claim 21, wherein after removal of the solvents, the catheter balloon is pleated, folded, and a sheath placed over the balloon, then optionally sterilized, and subsequently the catheter balloon is placed in a container of water, inflated to nominal pressure, and held for about 30 seconds at nominal pressure before removal; wherein for the particles comprising drug that are cast off the balloon during and after inflation, 30% or fewer have a diameter greater than 30 microns, based upon a volume average distribution.

38. The method of claim 27, wherein after removal of the solvents, the catheter balloon is pleated, folded, and a sheath placed over the balloon, then optionally sterilized, and subsequently the catheter balloon is placed in a container of water, inflated to nominal pressure, and held for about 30 seconds at nominal pressure before removal; wherein for the particles comprising drug that are cast off the balloon during and after inflation, 30% or fewer have a diameter greater than 30 microns, based upon a volume average distribution.

39. The method of claim 29, wherein after removal of the solvents, the catheter balloon is pleated, folded, and a sheath placed over the balloon, then optionally sterilized, and subsequently the catheter balloon is placed in a container of water, inflated to nominal pressure, and held for about 30 seconds at nominal pressure before removal; wherein for the particles comprising drug that are cast off the balloon during and after inflation, 30% or fewer have a diameter greater than 30 microns, based upon a volume average distribution.

40. The method of claim 38, wherein no further processing of the coating on the balloon is executed after removal of the solvents and before pleating and folding of the balloon.

41. The method of claim 39, wherein no further processing of the coating on the balloon is executed after removal of the solvents and before pleating and folding of the balloon.

* * * * *